US006239099B1

(12) United States Patent
Potempa

(10) Patent No.: US 6,239,099 B1
(45) Date of Patent: *May 29, 2001

(54) METHODS OF TREATING VIRAL INFECTIONS

(75) Inventor: Lawrence A. Potempa, Deerfield, IL (US)

(73) Assignee: Immtech International, Inc., Vernon Hills, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/767,795

(22) Filed: Dec. 17, 1996

Related U.S. Application Data

(63) Continuation of application No. 08/117,874, filed on Sep. 7, 1993, now Pat. No. 5,585,349, which is a continuation of application No. 07/799,448, filed on Nov. 27, 1991, now abandoned, and a continuation of application No. 08/480,270, filed on Jun. 7, 1995, now Pat. No. 5,874,238.

(51) Int. Cl.$^7$ .................................................. A61K 38/00

(52) U.S. Cl. ................................. 514/2; 514/12; 530/350

(58) Field of Search .......................... 514/2, 12; 530/350

(56) References Cited

U.S. PATENT DOCUMENTS

| 5,585,349 | 12/1996 | Potempa ................................. 514/12 |
| 5,593,897 | 1/1997 | Potempa et al. ..................... 436/507 |
| 5,874,238 | 2/1999 | Potempa et al. .................... 435/69.1 |

OTHER PUBLICATIONS

Ciampor, F., The Role of Cytoskeleton and Nuclear Matrix in Virus Replication, *ACTA Virol.*, 32:168–189 (1988).
Elliott, G. et al., Intercellular Trafficking and Protein Delivery by a Herpesvirus Structural Protein, *Cell* 88:223–233 (1997).
Fauci, A.S., The Human Immunodificiency Virus: Infectivity and Mechanisms of Pathogenesis, *Science* 239:617–622 (1988).
Fauci et al., Immunopathogenic Mechanisms in Human Immunodeficiency Virus (HIV) Infection, *Annals of Internal Medicine* 114:678–693 (1991).
Kabat et al., Antiretroviral Activity of a Recombinant Modified C–Reactive Protein, Twenty–First AIDS Clinical Trial Group Meeting, Jul. 1996, Abstract #14.
Karczewski M.K. et al., Cytoskeleton Association and Virion Incorporation of the Human Immunodeficiency Virus Type 1 Vif Protein, *Journal of Virology* 70:494–507 (1996).

Khattri et al., Anti–C–Reactive Protein Inhibits Cytoskeletal Rearrangement without Altering Calcium Influx in Natural Killer Cell Activation, *Cell Immunol.* 155:457–475 (1994).
Leão Ferreira et al., Rearrangement of intermediate filament network of BHK–21 cells infected with vaccinia virus, *Arch. Virol.* 138:273–285 (1994).
Motie, et al., Binding of Model Soluble Immune Complexes to Modified C–Reactive Protein, *J. Immunol.* 156:4435–4441 (1996).
Pepys et al., Binding of Pentraxins to Different Nuclear Structures: C–reactive Protein Binds to Small Nuclear Ribonucleoprotein Particles, Serum Amyloid P Component Binds to Chromatin and Nucleoli, *Clin. Exp. Immunol.* 97:152–157 (1994).
Potempa et al., Antigenic, Electrophoretic and Binding Alterations of Human C–Reactive Protein Modified Selectively in the Absence of Calcium, *Mol. Immunol.* 20:1165–1175 (1983).
Potempa et al., Expression, Detection and Assay of a Neoantigen (Neo–CRP) Associated with a Free, Human C–Reactive Protein Subunit, *Mol. Immunol.* 24:531–541 (1987).
Potempa et al., Stimulation of Human Neutrophils, Monocytes, and Platelets by Modified C–Reactive Protein (CRP) Expressing a Neoantigenic Specificity, *Inflammation* 12:391–405 (1988).
Potempa et al., Stimulation of Megakaryocytopoiesis in Mice by Human Modified C–reactive Protein, *Exp'l. Hematol.* 24:258–264 (1996).
Shoeman et al., Potential Role of the Viral Protease in Human Immunodeficiency Virus Type 1 Associated Pathogenesis, *Medical Hypotheses* 37:137–150 (1992).
Vaith, et al., Complement Activation by C–Reactive Protein on the HEp–2 Cell Substrate, *Int'l. Archives Allergy Immunol.* 111:107–117 (1996).
Belin & Boulanger, *J. Virol.*, 61(8):2559–2566 (1987).
Carvalhol, et al., *Virus Res.*, 11(2): 175–192 (1988).
Ciampor, *Acta Virologice*, 32(2) 168–89 (1988).

*Primary Examiner*—Dwayne C. Jones
*Assistant Examiner*—C. Delacroix-Muirheid
(74) *Attorney, Agent, or Firm*—Sheridan Ross P.C.

(57) ABSTRACT

The invention provides methods and compositions for treating viral infections in a mammal comprising administering a effective amount of modified C-reactive protein (CRP), $r_m$CRP or mutant CRP to the mammal. The viral infections treated are caused by viruses such as Herpes, papilloma, Epstein Barr and Retroviridae viruses. In particular, modified-CRP has been found to be effective and safe for treating retroviral infections, including human immunodeficiency virus 1. The invention also provides a method of neutralizing a virus comprising contacting the virus with the CRP compositions. In particular, modified-CRP can be used to neutralize viruses in blood which is to be used for transfusions by adding the modified-CRP to the blood prior to the transfusion.

2 Claims, 4 Drawing Sheets

OTHER PUBLICATIONS

Figure 1A:
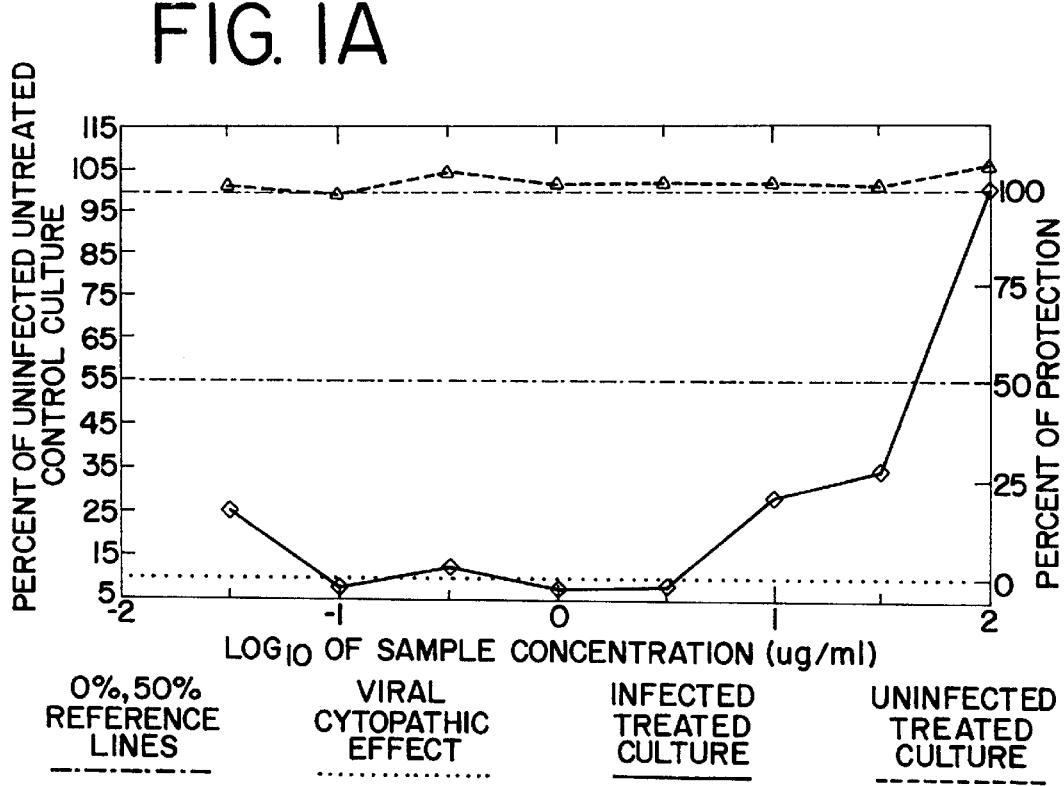

Crabbe, *Bioscience Reports*, 5(2):167–174 (1985).
Fauci, *Science*, 262:1011–1018 (1993).
Liao et al., *Exp. Cell. Res.*, 219:348–357 (1995).
Pantaleo & Fauci, *J. NIH Res.*, 5:68–72 (1993).
Pearce–Pratt et al., *J. Virol.*, 68(5):2898–2905 (1994).
Potempa et al., Abstract 1918, *FASEB J.*, 10:A1332 (1996).
Potempa et al., "In Vitro Studies of Recombinant Human Modified C Reactive Protein, An Active New Agent Against HIV Disease," Abstract B01, Hong Kong AIDS Conference, Nov. 1996.
Radosevich et al., Abstract 2688, *FASEB J.*, 10:A1466 (1996).
Virtanen et al., *Int. J. Cancer*, 42(2):256–260 (1988).
Wheeler et al., *J. Leukocyte Biol.*, 47(4):332–343 (1990).

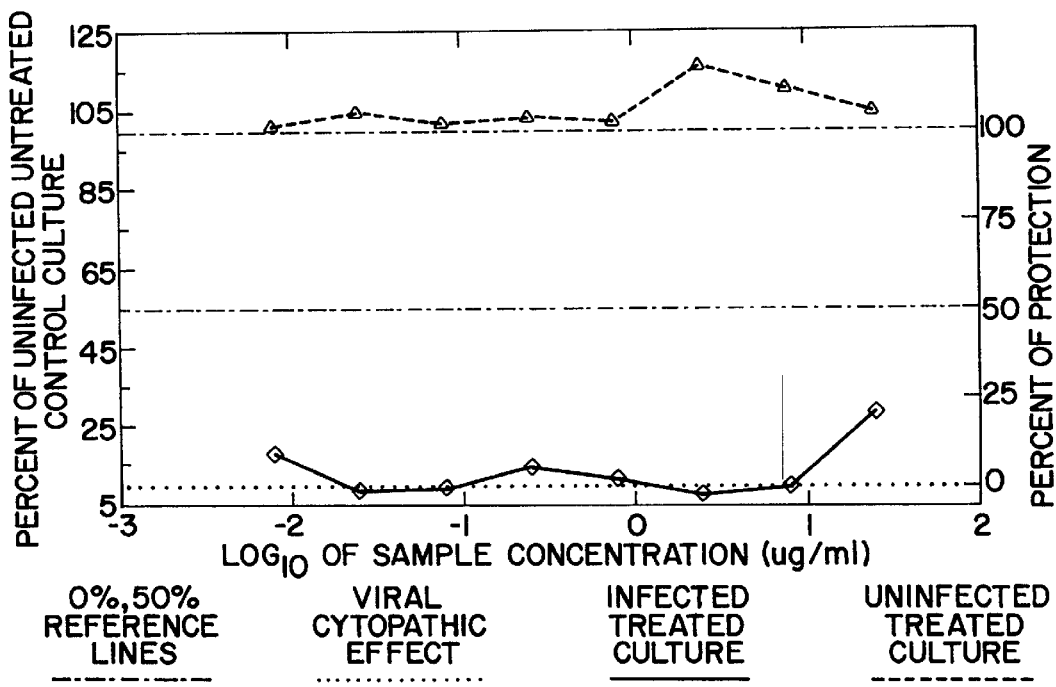
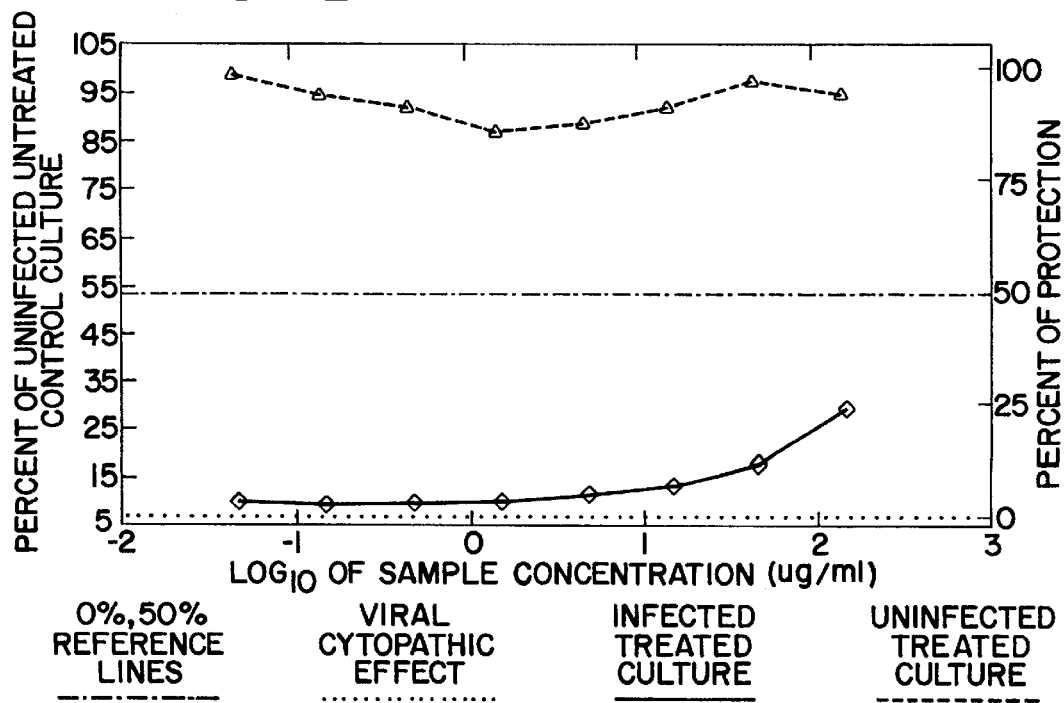

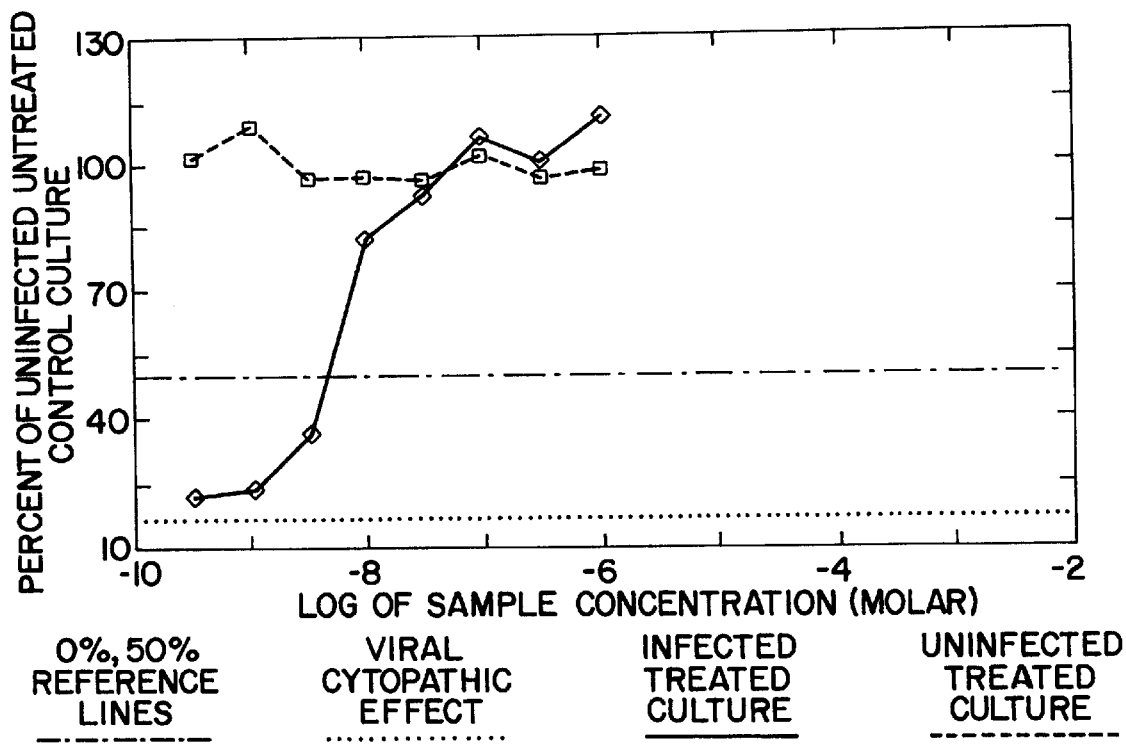

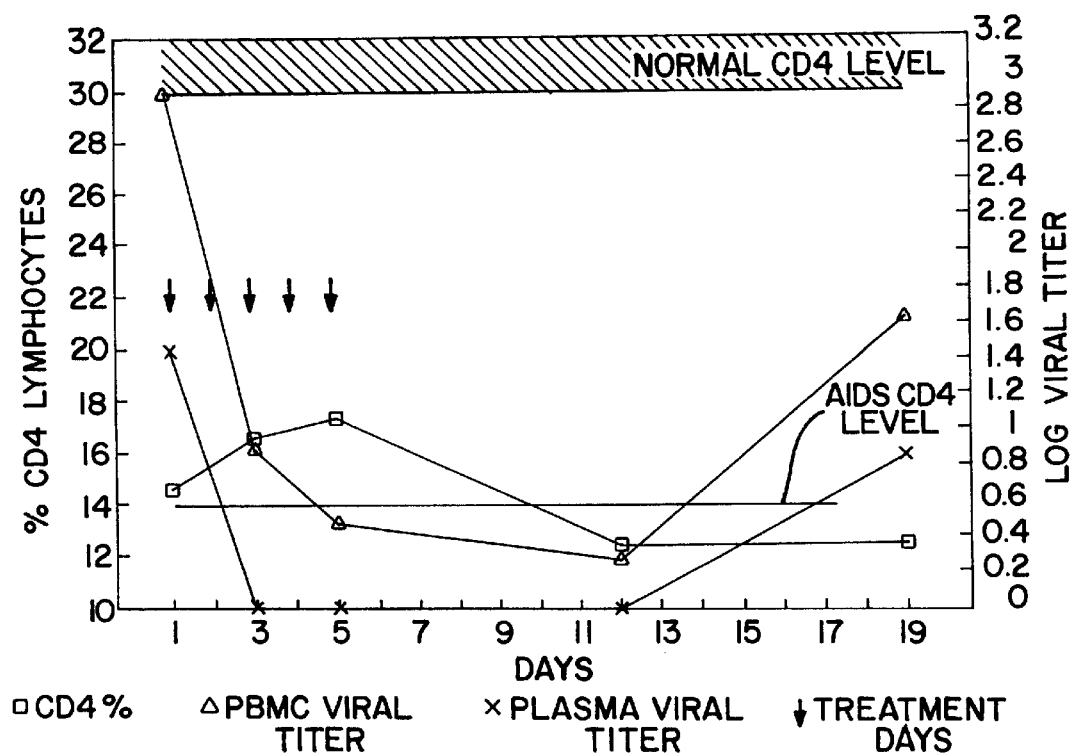
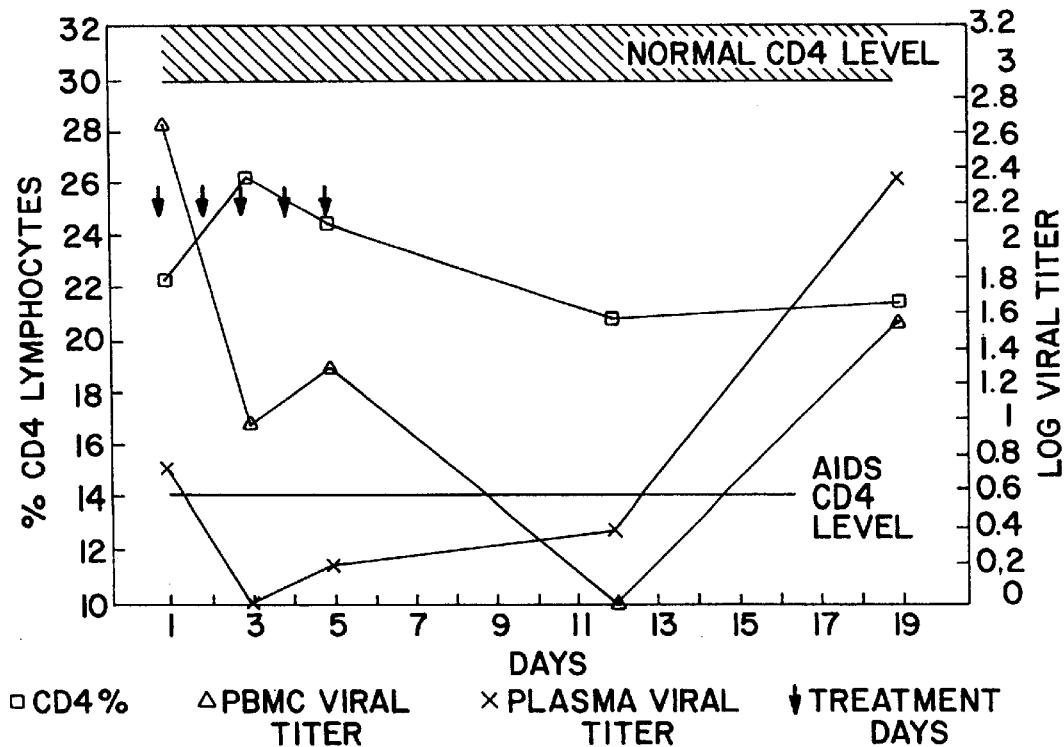

METHODS OF TREATING VIRAL INFECTIONS

This is a continuing application of U.S. Ser. No. 08/117,874 filed Sep. 7, 1993, now U.S. Pat. No. 5,585,349, which was a continuation under 37 CFR 1.62 of U.S. Ser. No. 07/799,448 filed Nov. 27, 1991, now abandoned; and of U.S. Ser. No 08/480,270 filed Jun. 7, 1995, now U.S. Pat. No. 5,874,238 incorporated herein by reference.

The invention relates to a method of treating viral infections with modified C-reactive protein (mCRP), mutant CRP and recombinant mCRP ($r_m$CRP).

Viral infections are serious human and veterinary health problems. Since the advent of AIDS (acquired immunodeficiency syndrome), the need for effective treatments for viral infections has become urgent. AIDS is caused by human immunodeficiency virus 1 (HIV-1). The initial pathogenic event is the binding of HIV-1 to the CD4 receptor on a subset of T cells and monocyte-macrophages. Fauci et al. (1991). The virus interacts with the human immune system, and the ultimate consequence of this interaction is a profound immunosuppression resulting from the quantitative depletion and functional abnormalities of the CD4 T-cell subset Mononuclear phagocytes may play a role in the pathogenesis of HIV-1 infection by serving as reservoirs of the virus. Of note is the fact that monocytes in the peripheral blood of HIV-1-infected individuals are rarely infected in vivo, whereas infected tissue macrophages may play a role in organ-specific HIV-1-related pathogenesis.

One drug that has been approved by the Food and Drug Administration (FDA) for the treatment of AIDS is 3'-azido-2',3'-dideoxy-thymidine (zidovudine, azidothymidine, AZT) which inhibits HIV-1 replication by acting at the level of reverse transcriptase. However AZT causes serious side effects, such as bone marrow suppression, and it is poorly tolerated in a high proportion of patients. (Yarchoan et al., 1990) Also, the beneficial effects of AZT have been reported to abate in 12–18 months. (Chase, 1988)

The FDA has also approved 2',3'-dideoxyinosine (DDI) for the treatment of AIDS in patients who cannot tolerate AZT or for whom AZT is no longer effective. DDI has been found efficacious and safe in the short-term, but its long term effects are not yet known.

Another drug for the treatment of AIDS is ampligen. Ampligen is a mispaired double-stranded RNA. It increases antiviral activity by stimulating interferon production, activating natural killer cells, and augmenting an internal cellular antiviral mechanism. (Montefiori et al., 1987; Dagani, 1987)

Other possible therapeutic approaches for the treatment of AIDS are discussed in Yarchoan et al. (1990); Dagani, (1987).

C-reactive protein (CRP) was first described by Tillett and Francis (1930) who observed that sera from acutely ill patients precipitated with the C-polysaccharide of the cell wall of *Streptococcus pneumoniae*. Others subsequently identified the reactive serum factor as protein, hence the designation "C-reactive protein."

In addition to binding to pneumococcal C-polysaccharide, CRP binds to: 1) phosphate monoesters including particularly phosphorylcholine; 2) other cell wall polysaccharides containing phosphorylcholine; 3) phosphatidyl choline (lecithin); 4) fibronectin; 5) chromatin; 6) histones; and 7) the 70 kDa polypeptide of the U1 small nuclear ribonucleoprotein. (Kilpatrick and Volanakis, 1991) Several laboratories have also reported the binding of CRP to galactose-containing polysaccharides. However, one laboratory has reported that CRP binds to trace phosphate groups that are minor constituents of one particular galactan, making it is unclear whether CRP binding to other galactans is also directed to phosphate residues or to carbohydrate determinants.

Atono (1989) teaches that the level of serum CRP is markedly increased in patients with acute hepatitis type A and type B, especially in type A, but decreases rapidly during the convalescent phase. The article also reports that the CRP level is generally low in non-A, non-B hepatitis in both the acute and convalescent phases.

Putto et al (1986) reports the results of measurements of the level of CRP in febrile children suffering from bacterial and viral infections. If the duration of the illness was more than 12 hours and the CRP level was less than 20 μg/ml, all children investigated had viral or probable viral infections. Some children with CRP levels of 20 μg/ml or less had invasive bacterial infections, but they had been sick for 12 hours or less. CRP levels between 20 μg/ml and 40 μg/ml were recorded in children with both viral and bacterial infections. A CRP value greater than, or equal to, 40 μg/ml detected 79% of bacterial infections with 90% specificity.

There have been no reports of CRP binding to viruses, contributing to the phagocytosis of viruses, or otherwise being able to neutralize viruses. CRP is not being used to treat viral infections.

Much of the study of CRP has been directed to determining its role in bacterial infections. For example, Xia et al. (1991) describes experiments designed to explore the role of CRP in endotoxin shock. A chimeric gene coding for rabbit CRP under the control of an inducible promoter (inducible in response to demand for gluconeogenesis) was introduced into mice. In contrast to most other vertebrates, mice synthesize only trace amounts of endogenous CRP, even during an acute phase response. When the chimeric gene was introduced into the mice, rabbit CRP was expressed in response to demand for gluconeogenesis. Further, it was found that 75% of mice expressing high levels of rabbit CRP following induction of gluconeogenesis survived treatment with 350–400 μg of endotoxin, as compared to 27% survival for animals in which rabbit CRP synthesis had been suppressed by inhibiting gluconeogenesis. The authors speculate that CRP may play a role in natural defense against endotoxin shock, although CRP is not known to bind endotoxin.

Mold et al. (1982) report that CRP binding can lead to complement activation and, in the presence of complement, enhancement of opsonization of C-polysaccharide-sensitized erythrocytes and type 27 *S. pneumoniae*. The article further reports that injections of CRP increased survival in mice challenged with type 3 or type 4 *S. pneumoniae*. Finally, the authors describe test results from which they conclude that CRP binds to a small group of potentially pathogenic gram-positive bacteria (*S. pneumoniae Streptococcus viridians*, and one isolate of *Staphylococcus aureus*), but does not bind to gram-negative bacteria or to other gram-positive bacteria. They, therefore, postulate that the ability of CRP to enhance opsonization and contribute to host defense may be specific for infection with *S. pneumoniae*.

Similarly, Mold et al (1982) report that CRP can act as an opsonin in the presence of complement. However, the article teaches that CRP does not bind to gram-negative bacteria and binds to only some gram-positive organisms. For those gram-positive bacteria to which CRP binds, the effectiveness of CRP as an opsonin varied depending on the species. Finally, the article reports that CRP protected mice from type 3 and type 4 *S. pneumoniae* infection.

Nakayama et al. (1983) also teach that CRP protects against lethal infection with type 3 or type 4 *S. pneumoniae*. The article further teaches that CRP did not protect against a similar dose of *Salmonella typhimunium* LT2.

Horowitz et al. (1987) describes the effects of CRP in mice with a X-linked immunodeficiency ("xid mice") which prevents the mice from making antibodies to polysaccharide antigens. In these mice, CRP provided protection against infection with type 3 *S. pneumonia* and acted by clearing the bacteria from the blood. However, CRP was not completely protective at higher doses of *S. pneumoniae*. Since CRP provides complete protection against these doses in normal mice, the authors speculated that the function of CRP is to slow the development of pneumococcal bacteremia until protective antibodies to capsular polysaccharide can be produced. C3 depletion decreased or abrogated the protective effects of CRP in xid mice, but not in normal mice.

Nakayama et al. (1984) reports the results of injecting mice with CRP and then immunizing them with type 3 *S. pneumococci*. The result was a diminished antibody response to the phosphorylcholine determinants on the bacteria which varied with the dose of CRP. However, antibodies were formed to other antigenic determinants on the *S. pneumococci*.

Hokama et al. (1962) report that carbonyl iron spherules, *Diplococcus pneumoniae* types IIs and XXVIIs and *Serratia marcescens* were phagocytosed more rapidly and in greater numbers by leukocytes of normal human blood after incubation with CRP. Similarly, Kindmark (1971) reports that CRP stimulated phagocytosis of *Diplococcus pneumoniae, Staphylococcus aureus, Escherichia coli* and *Klebsiella aerogenes*.

Gupta et al. (1986) teaches that CRP has been detected in immune complexes isolated from the sera of patients with acute rheumatic fever. Rheumatic fever is an acute inflammatory disease that may follow group A streptococcal pharyngitis. The other components of the immune complexes included streptolysin 0 and antibodies to streptolysin 0.

However Ballou et al. (1990) teaches that highly purified CRP does not bind to immunoglobulin (monomeric or aggregated) or immune complexes. The article suggests that the reported presence of CRP in immune complexes may result from, or be facilitated by, an association of CRP with components of the immune complexes other than immunoglobulin, such as antigens or complement components.

Kilpatrick and Volanakis (1985) report that there is a CRP receptor on stimulated polymorphonuclear leukocytes (PMN). The authors also disclose that the ingestion of erythrocytes coated with pneumococcal C-polysaccharide and CRP by activated PMN is greater than ingestion of erythrocytes coated only with pneumococcal C-polysaccharide. Finally, the authors propose that CRP's function relates to its ability to specifically recognize foreign pathogens and damaged or necrotic host cells and to initiate their elimination by 1) interacting with the complement system; or 2) interacting with inducible phagocytic receptors on neutrophils.

James et al. (1980) teaches that CRP binds a subset of mononuclear leukocytes, including 40% of the phagocytic monocytes and 3% of lymphocytes. Binding was influenced by several factors, including the form of the CRP molecule (i.e., modification of the CRP was required, either by complexing to a ligand or by heating to 63° C.).

Tebo et al. (1990) teach the presence of a receptor for CRP on monocytes. The article further discloses that a membrane receptor for CRP has been reported on neutrophils.

Kempka et al. (1990) disclose results which the authors interpret to mean that CRP is a galactose-specific binding protein which, when associated to the surface of liver macrophages, functions as a receptor mediating galactose-specific endocytosis of particulate ligands.

CRP is a pentamer which consists of five identical subunits. The pentameric form of CRP is sometimes referred to as "native CRP." In about 1983, another form of CRP was discovered which is referred to as "modified-CRP" or "mCRP". mCRP has significantly different charge, size, solubility and antigenic characteristics as compared to native CRP. mCRP also differs from native CRP in binding characteristics; for instance, mCRP does not bind phosphorylcholine. Finally, mCRP differs from native CRP in its biological activity.

The distinctive antigenicity of mCRP has been referred to as "neo-CRP." Neo-CRP antigenicity is expressed on:
1) CRP treated with acid, urea or heat under certain conditions (described herein);
2) the primary translation product of DNA coding for CRP (preCRP); and
3) CRP immobilized on plastic surfaces.

A molecule reactive with polyclonal antibody specific for neo-CRP has been identified on the surface of 10–25% of peripheral blood lymphocytes (predominantly NK and B cells), 80% of monocytes an 60% of neutrophils, and at sites of tissue injury. In addition, it has been reported that CRP can influence the development of monocyte cytotoxicity, improve the accessory cell function of monocytes, potentiate aggregated-1gG-induced phagocytic cell oxidative metabolism, and increase the production of interleukin-1, prostaglandin E and lipoxygenase products by monocytes.

Chudwin et al. (1986) teach that mCRP can have a protective effect in mice challenged with gram-positive type 7F *S. pneumoniae*. Mice were injected intravenously with saline, native CRP, or mCRP. Thirty minutes later the mice received a lethal dose of *S. pneumoniae*. Survival at 10 days was as follows: 2/18 mice pretreated with saline; 7/12 mice pretreated with 200 µg of CRP; 12/18 mice pretreated with 10 µg CRP; and 5/6 mice pretreated with 100 µg of mCRP. The authors speculate that CRP may be protective against bacterial infections by mechanisms other than phosphorylcholine binding and that CRP may have a wider role in bacterial host defenses than previously suspected by being changed into the mCRP form of the molecule (mCRP does not bind phosphorylcholine).

There have been no reports that mCRP is protective against any other kind of bacterial infection. There have been no reports of mCRP binding to viruses, contributing to the phagocytosis of viruses, otherwise being able to neutralize viruses, or being used to treat viral infections.

For reviews of CRP and mCRP, see Gotschlich (1989); U.S. Pat. Nos. 5,272,258; 5,283,238; 5,474,904; 5,547,931.

The mCRP antigen is naturally expressed not as a serum factor, but as a tissue-associated factor deposited within certain areas of the extracellular matrix (ECM). mCRP antigens are naturally expressed in the intima, media and adventitia of healthy blood vessels, in fibrous tissues of the skin, and in structural architectural regions of the lymph and the spleen.

An antigen cross-reactive with mABs to mCRP has been located inside cells in association with the cytoskeleton. Also, using human epithelial cell substrates, mCRP specifically bound to intracellular fibrous proteins believed to be intermediate filaments (Vaith et al., 1996). The intracellular fibrous structural matrix (termed the cytoskeleton) is made up of three main types of proteins-microtubules (MT), actin and intermediate filament (IFs). All three types radiate throughout the cell cytoplasm where, together with intermediary linker proteins, they respond to plasma membrane signals initiated by ligand/receptor interactions, and reversibly aggregate and dissociate, controlling cellular extension and contraction activities fundamental to growth and movement, and controlling the distribution of intracellular granules fundamental to cellular function.

The cytoskeleton intracellular matrix proteins are crucial factors which regulate not only individual cell structure/function activities, but also the interaction with, movement through, and coordinated activities of each cell with other cells and with the extracellular matrix (ECM). The IF cytoskeletal proteins are central to this communication network as they polymerize in a directed manner from the nuclear membrane outward to the plasma membrane. Along the length of IF fibers within the cytoplasm, intermediate filament associated proteins (IFAPs) and chaperone proteins help regulate the dynamic polymerization/depolymerization activities of IFs which, in turn, affects the distribution and activities of other cytoskeletal proteins and the organization, movement and activities of cytoplasmic organelles. Viral particles and certain RNA molecules can directly associate with intermediate filament cytoskeletal proteins.

Any agent which alters the equilibrium between polymerization and depolymerization reactions of the cytoskeleton can "transform" a cell into a state of hyperactivity. With reference to HIV disease, it has been recently shown that the HIV-1 protease has, as a substrate, a variety of host cell cytoskeletal proteins (Shoeman et al. 1992) The significance of this was summarized on page 145 of this article, "the cytoskeleton represents a potential physical barrier to virus entry, to transport of the viral genome into the nucleus and to release of viral particles from the cell surface during replication. Disruption of the cytoskeleton may be a physical requirement for a budding virus (and indeed is observed in other viral systems such as vesicular stomatitus virus, human respiratory syncytial virus and simian virus 40 . . . )" It follows that the capacity of a virus to control the degradation of the host cell cytoskeleton proteins may be advantageous for the general survival and propagation of the virus (i.e., natural selection mechanisms).

There are known drugs which bind to or otherwise influence components of the cytoskeleton (e.g., cytochalasins, vinblastin/vincristin, taxol). These agents are therapeutically active because they effectively arrest cell hyperactivity. All currently used cytoskeleton-specific drugs are known to specifically target either the actin cytoskeleton protein or the tubulin (i.e., microtubule) cytoskeleton protein.

SUMMARY OF THE INVENTION

The invention provides a method of treating viral infection in a mammal comprising administering to the mammal an effective amount of modified-CRP, mutant-CRP or recombinant CRP ($r_m$CRP), in a pharmaceutically-acceptable carrier. Viral infections include those caused by Herpes, Retroviridae, papilloma. In particular, modified-CRP has been found effective in treating Retroviridae infections, including human immunodeficiency virus 1 (HIV-1) infections.

The mutant protein has the same amino acid sequence as an unmutated CRP subunit or an unmutated preCRP, except that at least one amino acid of the unmutated CRP subunit or unmutated preCRP has been deleted, at least one amino acid of the unmutated CRP subunit or unmutated preCRP has been replaced by another amino acid, at least one amino acid has been added to the unmutated CRP subunit or unmutated preCRP, or a combination of such changes has been made. The amino acid(s) added, deleted and/or replaced are chosen so that the mutant protein is less likely to form covalently cross-linked aggregates than the unmutated CRP or unmutated preCRP. The mutant protein also exhibits at least one of the biological activities of mCRP.

The invention further provides a DNA molecule coding for the mutant protein of the invention and a vector for expression of the mutant protein. The vector comprises a DNA sequence coding for a mutant protein of the invention operatively linked to expression control sequences.

The invention also provides a method of neutralizing a virus comprising contacting the virus with modified/CRP. For instance, modified-CRP can be used to neutralize viruses in a blood sample which is to be used for a transfusion by adding the modified-CRP to the blood sample prior to the transfusion. In particular, modified-CRP has been found effective in neutralizing Retroviridae, including HIV-1.

mCRP and $r_m$CRP are therapeutically active compounds which can affect both virally-induced and malignant cell hyperactivity. mCRP and $r_m$CRP elicit their therapeutic effects in part by specifically targeting intermediate filaments and hence, by controlling some aspect of cell hyperactivity. The net result of a cell that is stronger because MCRP and $r_m$CRP improve cell structure (morphology), distribution and metabolic activity, is a reduced propagation of virus. mCRP and $r_m$CRP are "cytoskeleton binding" and "cell-structure altering." mCRP may be an intermediate filament associated protein (IFAP). By affecting the structure and function aspects of the cell that a virus needs to infect and proliferate, mCRP or $r_m$CRP have unique anti-viral activities which are not directed to specific virus and viral enzymes. Hence, the therapeutic activities of mCRP in viral infection are not limited to specified viral types such as HIV. It is likely that mCRP and $r_m$CRP are the first therapeutic agents of any kind which can be used to influence the functional activities of intermediate filament cytoskeletal proteins.

BRIEF DESCRIPTION OF THE DRAWINGS

FIGS. 1A and 1B are graphical representations of the results of two in vitro formazan assays for activity of an mCRP suspension against HIV-1.

FIGS. 1C and 1D are graphical representations of the results of two in vitro formazan assays for activity of soluble mCRP against HIV-1.

FIG. 1E is a graphical representation of the results of an in vitro formazan assay for activity of AZT against HIV-1.

FIGS. 2A and 2B are graphical representations of percent CD4 lymphocytes and $\log_{10}$ of SIV titer in peripheral blood mononuclear cells (PBMC) and plasma for monkey 2B (FIG. 2A) and monkey 50B (FIG. 2B) versus time; the arrows indicate the days on which CRP was administered to the monkeys.

DETAILED DESCRIPTION OF THE PREFERRED EMBODIMENTS

The modified-CRP useful in the practice of the invention may be from any species. There is substantial homology between the amino acid sequences of CRP's from different species. For instance, there is from about 50 to about 80% sequence homology between CRP's from various mammalian species (Hu et al., 1986; Whitehead et al., 1990). It is, therefore, expected that mCRP from any species will be effective in treating viral infections or neutralizing viruses. Thus, a mammal suffering from a viral infection may be treated with mCRP from a different species (e.g., mice can be treated with human mCRP). Alternatively, and preferably, the mammal is treated with homologous mCRP (e.g., humans are treated with human mCRP) to avoid immune reactions to the mCRP.

mCRP is preferably made using CRP as a starting material. Methods of isolating CRP from natural sources are well known. Many such techniques are described in the references discussed in the Background section. CRP is preferably isolated from pleural or ascites fluid by calcium-dependent affinity chromatography using phosphorylcholine-substituted BioGel A 0.5 m (an agarose-based resin obtained from BioRad Laboratories) as described by Volanakis et al. (1978) and modified by Potempa et al. (1987). Using this procedure, CRP can be obtained which is at least 99% pure.

Genomic and CDNA clones coding for human, mouse, and rabbit CRP have been isolated (Lei et al., 1985; Woo et al., 1985; Hu et al., 1985, 1988). Given the substantial homology between CRP's from different species, probes can readily be prepared so that genomic and cDNA clones can be isolated which code for CRP's from other species. Methods of preparing such probes and isolating genomic and cDNA clones are well known. Using one of the known clones or a newly-isolated clone, CRP can be prepared using conventional and well known recombinant DNA techniques and cell culture and fermentation conditions. However, to obtain pentameric native CRP, eukaryotic host cells, preferably mammalian host cells should be used (Samols and Hu, 1986; Hu et al., 1988).

Methods of making mCRP from CRP are well known. Many such methods are described in the references discussed in the Background section. For instance, mCRP can be prepared by denaturing CRP. CRP can be denatured by treatment with an effective amount of urea (preferably 8M) in the presence of a conventional chelator (preferably ethylenediamine tetraacetic acid (EDTA) or citric acid). Further, CRP can be treated to produce mCRP by adjusting the pH of the protein to below about 3 or above about 11–12. mCRP can also be produced by heating CRP above 50° C. for a time sufficient to cause denaturation (preferably at 63° C. for 2 minutes) in the absence of calcium or in the presence of a chelator such as those listed above.

mCRP can also be prepared using recombinant DNA techniques. As noted in the Background section, the primary translation product of the CRP gene (preCRP) has been found to express neo-CRP antigenicity. Accordingly, mCRP can be prepared by selecting conditions so that that the CRP subunits are not assembled into pentameric native CRP in the host cell. This can be accomplished by expressing the desired genomic or cDNA clone in a prokaryotic host. The mCRP produced in this manner appears to consist of aggregates of CRP subunits and/or preCRP and perhaps other CRP peptides. This form of mCRP is insoluble, and further purification is problematical. However, it should be possible to inject this insoluble material directly into mammals as a suspension without further processing since suspensions of isolated mCRP prepared from CRP have been found safe and effective when injected into mammals (see Example 2).

Finally, mCRP can be prepared by adsorbing CRP to hydrophobic solid surfaces. Suitable solid surfaces and conditions are described in co-pending application Ser. No. 07/271,137 and EPO issued U.S. Pat. No. 0,411,017, the disclosures of which are incorporated herein by reference.

mCRP adsorbed to solid surfaces may be useful in removing viruses from fluids, such as blood, as discussed below.

mCRP may be distinguished from native CRP by several criteria. As noted in the Background section, modified CRP expresses neo-CRP antigenicity, whereas native CRP does not. Neo-CRP antigenicity can be detected using polyclonal antisera specific for neo-CRP as described in the Background section. Preferably, however, mCRP is distinguished from native CRP using monoclonal antibodies like those described in U.S. Pat. No. 5,272,258, the disclosure of which is incorporated herein by reference. These monoclonal antibodies are also described in Ying et al. (1989). mCRP also binds immune complexes and aggregated immunoglobulin, whereas native CRP does not as described in co-pending application Ser. No. 08/271,137 issued on Jan. 17, 1997 as U.S. Pat. No. 5,593,897 and issued EPO Pat. No. 0,411,017. There are also several other ways to distinguish mCRP from native CRP including charge, solubility, binding characteristics and biological activity as discussed in the Background section. However, to show that a preparation contains mCRP, it is usually sufficient to establish that the preparation 1) reacts positively with an antibody specific for an epitope found only on mCRP and 2) binds aggregated immunoglobulin (e.g., aggregated lgG).

Although not wishing to be bound by any particular theory, it is believed that mCRP is formed by the dissociation of the five CRP subunits, each of which then undergoes a spontaneous conformational change to form mCRP (Bray et al., 1987). Accordingly, it is possible that fragments of the CRP subunits may have the same activities described herein for mCRP, and the use of such fragments would come within the scope of the present invention.

mCRP can bind with certain intracellular fibrous structures which, based on the distribution pattern inside the cell, are believed to be intermediate filaments (IFs). A photograph showing the distribution of mCRP when overlaid on human epithelial cells (i.e. HEp-2 cells) is shown in Vaith et al. (1996), which presents a mechanism for mCRP activity. The top plate shows the distribution of mCRP as detected with a monoclonal antibody to mCRP (mAb anti-mCRP 9C9), and the bottom plate shows the distribution of mCRP detected with a polyclonal antibody which has specificity for both native CRP and mCRP. Intermediate filaments have an intracellular distribution which surrounds the cell nucleus and radiates outward toward the plasma membrane. This photograph shows the primary circa-nuclear staining observed with mCRP reagents. Binding of native CRP to HEp-2 cells is distinct, being found within the nucleus in a punctate granular pattern. Native-CRP binds to nuclear, not to cytoplasmic structures (DuClos, 1989; Pepys et al., 1994).

Data shows that mCRP antigens are naturally expressed in the cytoplasm of all peripheral blood leukocytes, and in tissue fixed lymphocytes, endothelial and epithelial cells. This was found in two ways. First, peripheral blood mononuclear cells were isolated from people using standard Ficoll techniques. When monoclonal antibodies specific for MCRP were added to such intact cells, with detection of bound antibody achieved using fluorescence technology, little or no staining was found. Using two color flow cytometry, a small level of mCRP antigen was naturally found on the surface of monocytes and neutrophils, but essentially no mCRP was found on the surface of lymphocytes (Potempa et al., 1996).

If this same cell population was permeabilized after Ficoll-purification, using commercial permeabilizing agents (e.g., Becton-Dickenson's FACS lyse solution or Immunotech's Lyse and Fix Reagent), the mCRP antigen was found strongly expressed in the cytoplasm of each of the T-lymphocyte, B-lymphocyte, monocyte and neutrophil populations. Essentially all the cells stained positive for the mCRP antigen.

The second way the mCRP antigen was found associated with the cytoplasm was by using immunohistochemical techniques. When solid human tissues were collected and stained for the presence of the mCRP antigen with the anti-mCRP mAb 9C9, the distribution of the mCRP antigen in the cytoplasm of lymphocytes was verified. When sections of a normal tonsil lymph node were processed using immunohistochemical antigen-recovery techniques (i.e., heating paraffin-prepared tissue sections prior to staining with antibody), strong cytoplasmic (and not nuclear) staining pattern in B-cells (predominantly within the germinal center) and T-cells (in the paracortical area where there is a mixture of T-cells and B-cells were seen). Of note, when the germinal center is viewed under a higher magnification, the tissue fixed macrophages do not appear to stain. This is different from the blood-borne precursor of tissue-fixed macrophage (the monocyte) and may have a functional relevance as a macrophage is, in one sense, an activated form of a peripheral blood monocyte.

Further proof of lymphocyte cytoplasmic staining was provided in a tissue section taken from a patient with colon adenocarcinoma. This tissue was prepared as a frozen section and was stained with a different anti-mCRP mAb (8C10) which reacts with mCRP at an epitope distinct from where mAb 9C9 reacts Ying et. al; 1992. Cytoplasmic staining of the lymphocytes is strongly shown. Since two distinct methods for preparing tissues and two distinct mAbs to mCRP reacted with a similar cytoplasmic distribution in lymphocytes, the probability that it is the mCRP antigen present and not a cross-reactive antigen is greatly enhanced.

mCRP is found in the cytoplasm of those cells known to be the primary target for HIV propagation-T-lymphocytes and monocytes. In the cytoplasm, mCRP binds to the cytoskeleton, a structure which must be altered for viral propagation. Because mCRP has the capacity to effectively stop HIV from killing cultured cells, one way that mCRP may elicit this anti-HIV effect is by helping maintain a strong cytoskeleton which cannot be easily cleaved by the HIV-protease. This, in essence, boosts the host's innate (acute phase) protective mechanism against viral disease by strengthening a natural physical barrier to viral propagation, hence suppressing the proliferation of HIV. It follows that since mCRP affects the host cell rather than the virus, therapeutic use of mCRP should be effective in other viral diseases as well.

It is also contemplated that proteins substantially homologous to CRP will have the activities described herein for mCRP. Such proteins are also considered to be within the scope of the invention. For instance, CRP subunits having a few amino acids added, deleted or substituted by, e.g., site-directed mutagenesis of the CRP gene (see definition of mutant CRP herein), and could be substituted for mCRP in the treatment of viral infections. In particular, mCRP is defined herein to include the primary translation product of the CRP gene.

Because of its action to influence the protective barrier of the cellular cytoskeleton, mCRP can be used to treat any type of viral infection. However, it is particularly noteworthy that mCRP has been found effective and safe in treating Retroviridae infections. mCRP has been found to provide significant protection against HIV-1 infection in the standardized in vitro test performed by the National Cancer Institute (NCI), while exhibiting no toxicity at any dose tested. mCRP has also been found to significantly reduce simian immunodeficiency virus (SIV) titers and increase the number of CD4 cells in monkeys in a manner comparable or superior to AZT, but without any side effects.

The Retroviridae are a family of spherical enveloped RNA viruses comprising three sub-families: Oncovirinae, Spurmavirinae and Lentivirinae. The particles are 80–100 nm in diameter with glycoprotein surface projections of 8 nm. Replication starts with reverse transcription of virus RNA into DNA which becomes integrated into the chromosomal DNA of the host. Endogenous oncoviruses occur widely among vertebrates and are associated with many diseases. Transmission is both vertical and horizontal.

The lentiviruses include HIV-1 and SIV. (Fauci (1988) Of particular note are HIV-1's morphological, biological and molecular similarities to the visna virus of sheep, to the equine infectious anemia virus, and to the feline immunodeficiency virus. HIV-1 is also related to other primate retroviruses such as STLV-Ill (believed to be the same as SIV). HIV-2 shares serological reactivity and polynucleotide sequence homology with STLV-III and has been isolated from West African patients with a clinical syndrome indistinguishable from HIV-1-induced AIDS and AIDS-related condition (ARC).

To treat viral infections in a mammal, an effective amount of mCRP mutant CRP or $r_m$CRP (hereinafter "mCRP") is administered to the mammal. The mCRP is preferably administered to the mammal before the infection becomes too serious. Most preferably, the mCRP is administered at the first indication of a viral infection or prophylactically to those at risk of developing viral infections. For instance, mCRP may be administered prophylactically to hemophiliacs or surgical patients who may receive blood contaminated with a virus such as HIV-1. Indeed, it is contemplated that mCRP can be added to blood bags, preferably at the time that blood is drawn, to neutralize any viruses, especially HIV-1, which may be present in the blood and to, thereby, prevent transmission of the virus to those who receive transfusions. Of course, mCRP can be administered to a mammal already suffering from a viral infection.

mCRP will generally be administered to the mammal by injection (e.g., intravenous, intraperitoneal, subcutaneous, intramuscular) or encapsulated in liposomes. Preferably intravenous injection is used. mCRP may also be applied topically to, e.g., a wound or other site of infection. Finally, it should be possible to administer mCRP by means of a spray to treat respiratory infections. It should be noted that it is unlikely that mCRP can be administered orally since it is a protein.

It is understood by those skilled in the art that the dose of mCRP that must be administered will vary depending on the mammal which will receive the mCRP, the type of infection, the seriousness of the infection, the route of administration, and the identity of any other drugs being administered to the mammal. It is also understood that it may be necessary to give more than one dose of mCRP.

Effective dosages and schedules for administration of mCRP may be determined empirically, and making such determinations is within the skill of the art. A suitable dose from about 5 $\mu$g to about 150 mg of mCRP per kg, preferably from about 250 $\mu$g to about 15 mg per kg is effective for treating viral infections. Generally, several such doses of mCRP must be given to the mammal, and the interval between doses is preferably from about 1 day to about 7 days. Administration of mCRP should be continued until health has been restored to the mammal.

Pharmaceutically-acceptable carriers are well known. For instance, suitable carriers for the administration of mCRP include fluids such as water, saline and buffers. Preferably, phosphate buffered saline, pH 7.4, is used as the carrier. mCRP may also be administered encapsulated in liposomes Deodhar et al. (1982); Thombre etal. (1984); Bama et al. (1984)]. For topical application, mCRP may be incorporated into lotions, gels, creams, and the like.

A mechanism by which mCRP exerts its effects involves the cell cytoskeleton. A number of viruses (e.g., HIV-1, vesicular stomatitis virus, human respiratory syncytial virus, simian virus 40) need to alter or disrupt the cytoskeleton in order to propogate. mCRP exerts its antiviral effects by acting or interacting with the host cells and/or the immune system of the mammal to make it more effective in coping with the viral infection. In addition, it is highly likely that mCRP binds to viruses.

mCRP is used in an assay for detecting or quantitating viruses. mCRP is used in assays such as those described in copending application Ser. No. 07/582,884. For example, mCRP is bound to a solid surface and used to bind virus in a body fluid. After washing away unbound material, the virus is detected or quantitated using a labeled antibody to the virus. Alternatively, the antiviral antibody is bound to the solid surface, and the mCRP is labeled.

mCRP is also suitable to neutralize viruses present in fluids such as blood. As noted above, it is contemplated that mCRP can be added to blood bags, preferably at the time that blood is drawn, to neutralize any viruses, especially HIV-1, which may be present in the blood and to, thereby, prevent transmission of the virus to those who receive transfusions. Preliminary data from experiments in which mCRP was added to blood to which HIV-1 was subsequently added indicate that mCRP reduced infectivity. Alternatively, mCRP could be bound to a solid surface, such as in a plasmapheresis device, as described in co-pending application Ser. No. 07/582,884, and blood or other fluid can be passed through the device to remove the virus.

The effects of adding $r_m$CRP to both HIV-infected and uninfected cultured MT-2 human lymphocytic cell lines are that $r_m$CRP caused both uninfected and infected cells to 1) change morphology- assuming a more normal size, shape, and distribution, and 2) increase metabolic activity (as measured in a formazan assay) to about twice that seen in untreated cells. In addition to the effect of $r_m$CRP on the morphology/activity of cultured lymphocytic cell lines, $r_m$CRP (mCRP) has been shown to have similar effects on megakaryocytes (see U.S. Pat. No. 5,547,931), and on a THP-1 cultured human monocyte cell line.

Viruses that form, or are expressed at sites of skin surface lesions such as infectious sores, cuts, abrasions or burns (e.g. Herpes simplex, papilloma, Epstein Barr virus), are treated with topical application of mCRP or $r_m$CRP. $r_m$CRP strengthens the tissues and cells which the virus has infected or is trying to infect, resulting in a "generic" therapeutic anti-viral affect. mCRP is part of the primitive (innate) non-specific immune system. Anatomical barriers and non-specific inhibitors are key natural elements which control the spread and propagation of many types of viruses.

Finally, it is contemplated that mCRP can be used as an adjuvant in vaccines designed to elicit protection against viruses. The ability of mCRP to neutralize viral infectivity should make such vaccines safer.

EXAMPLES

Example 1

Activity of Modified CRP Against HIV-1 In Vitro

A Preparation of Modified-CRP

Human CRP was isolated from pleural or ascites fluid by calcium-dependent affinity chromatography using phosphoryl choline-substituted BioGel A 0.5 m (an agarose-based resin obtained from BioRad Laboratories) as described by Volanakis et al. (1978). Briefly, the pleural or ascites fluid was passed over the phosphorylcholine-substituted column, and the CRP was allowed to bind. Then, the column was exhaustively washed with 75 mM Tris HCl saline (pH 7.2) containing 2 mM $CaCl_2$ until the absorbance at 280 nanometers was less than 0.02. The CRP was eluted with 75 mM Tris, 7.5 mM citrate-buffered saline (pH 7.2). This high concentration of Tris significantly reduces non-specifically adsorbed proteins which often contaminate affinity-purified CRP preparations.

CRP-containing fractions were pooled, diluted three-fold with deionized water, adsorbed to DE52 ion exchange resin (from Whatman), and then eluted with a linear salt gradient of from 0.05 M to 0.5 M NaCl. CRP-containing fractions were pooled and re-calcified to 2–5 mM $CaCl_2$ (by adding a suitable amount of a 1M solution) and applied to unsubstituted Biogel A 0.5 m column to remove residual serum amyloid P component (SAP).

Next, the CRP was concentrated to 1 mg/ml using ultrafiltration (Amicon; PM30 membrane) under 10 psi nitrogen. A CRP extinction coefficient (μg/ml) of 1.98 was used to determine concentration. Next, the concentrated CRP was exhaustively dialyzed in 10 mM Tris-HCl-buffered saline (pH 7.2) containing 2 mM $CaCl_2$, sterile-filtered and stored at 4° C. These preparations produced a single Mr 23,000 band on SDS-PAGE electrophoresis and were more than 99% free of SAP, lgG and all other proteins tested for antigenically.

To make mCRP, the CRP (prepared as described above) at 1 mg/ml was incubated in 8 M ultra-pure urea (Schwartz-Mann, Spring Valley, N.Y.) in the presence of 10 mM EDTA for one hour at 37° C. The urea was removed by dialysis into 10 mM sodium phosphate buffer (pH 7.4) or Tris-HCl buffer (pH 7.2) containing 0.015 M sodium chloride; more than 90% of the starting protein was accounted for in the solution phase after dialysis.

The mCRP was sterile filtered through a 0.20 micron filter (Gelman). The concentration was then adjusted to 0.5 μg/ml with 10 mM sodium phosphate buffer, pH 7.4, containing 0.015 M sodium chloride to produce a solution of mCRP. This solution is referred to herein as "soluble mCRP".

Some of the sterile-filtered soluble mCRP was adjusted to physiologic ionic strength by adding sodium chloride to give a final concentration of 0.15 M NaCl and then incubated in an ice bath for 15 minutes. The majority of the mCRP self-aggregated to form an opalescent suspension which was centrifuged at about 5000×g for 10 minutes to sediment the protein. The sedimented protein was resuspended in an appropriate volume of sterile buffer (preferably 10 mM sodium phosphate buffer, pH 7.4, containing 0.15M NaCl) to give a final concentration of mCRP of 2–4 mg/ml. This suspension is referred to herein as "mCRP suspension".

B. In Vitro Assay

Soluble mCRP and mCRP suspension, prepared as described in Part A, were submitted to the National Cancer Institute, (NCI) for testing in their standardized in vitro assay for activity against HIV-1. The assay used by the NCI is that described in Weislow et al. (1989). This procedure is designed to detect agents acting at any stage of the virus reproductive cycle. Agents that interact with virions, cells, or virus gene-products so as to interfere with viral activities will protect cells from cytolysis.

Briefly, the assay was performed as follows. Serial dilutions of mCRP in cell culture medium were prepared. T4 lymphocytes (CEM cell line) were added and, after a brief interval, HIV-1 was added. The cultures were incubated at 37° C. in a 5% carbon dioxide atmosphere for 6 days. Then a tetrazolium reagent (2,3-bis[2-methoxy-4-nitro-5-sulfophenyl]-5-[(phenylamino)carbonyl]-2H-tetrazolium hydroxide) was added to all wells and the cultures were incubated to allow formazan color development by viable cells. Individual wells were analyzed spectrophotometrically to quantitate formazan production, and were viewed microscopically to detect viable cells and confirm protective activity. Virus-infected cells treated with mCRP were compared with uninfected cells treated with mCRP (toxicity control) and with other appropriate controls (untreated infected, untreated noninfected cells, mCRP wells without cells, etc.) on the same plate. All tests were compared with a positive control (AZT-treated) done at the same time under identical conditions.

The results of the assay are shown in FIGS. 1A–E. In those figures, the solid line connecting the diamond symbols depicts the percentage of surviving HIV-1 infected cells treated with mCRP or AZT relative to uninfected, untreated controls. The dashed line connecting the triangular symbols depicts the percentage of surviving uninfected cells treated with mCRP or AZT relative to the same uninfected, untreated controls (toxicity control). The viral cytopathic effect is indicated by the dotted reference line. This line shows the extent of destruction of cells by the virus in the absence of treatment and is used as a quality control parameter. Survival values of this parameter less than 50% are considered acceptable. The percent of protection is presented on the right side of the graph.

Figure 1B:
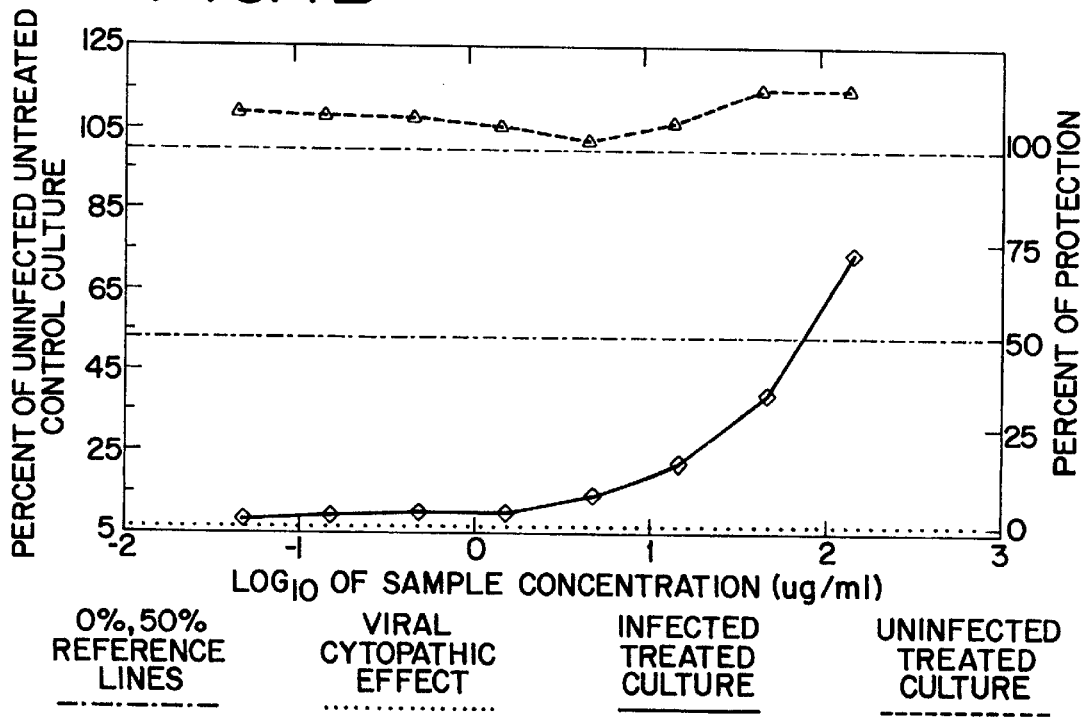

As is shown in FIGS. 1A–1D, mCRP had excellent anti-HIV-1 activity. mCRP gave as much as 73–100% protection at 100–150 $\mu$/ml (see FIGS. 1A and 1B). Also, mCRP exhibited little or no toxicity for the T4 cells at any dose tested.

An approximate value for 50% effective concentration ($EC_{50}$) was calculated by NCI as 45 $\mu$g/ml. The 50% inhibitory concentration ($IC_{50}$) could not be calculated since little or no inhibition by mCRP alone was detected. These results compare very favorably with those obtained with the AZT control (see FIG. 1E).

Example 2

Use of Modified-CRP to Treat an SIV Infection in Monkeys mCRP was tested in vivo for activity against simian immunodeficiency virus (SIV). Two male rhesus (*Macaca mulatta*) monkeys (designated 2B and 50B) having an established SIV infection were used. They both had been given approximately 1000 $TCID_{50}$ SIVmac251 virus about 10 months before treatment with mCRP was begun. They had been treated unsuccessfully with another experimental drug (identity unknown), but they had received no treatments of any kind for at least one month before being given mCRP to "wash out" the other drug.

Each monkey was given an intravenous injection of 16 mg of mCRP suspension (prepared as described in Example 1, part A) each day for 5 consecutive days (for a total of 80 mg/5.5–5.9 kg monkey). The first day of treatment was designated day 1.

Clinical observations were performed once daily for 19 days. Complete physical examinations were performed on day 1 prior to treatment and on day 19. Limited physical examinations (temperature, pulse and respiration) were performed on days 3, 5 and 12.

Blood samples were drawn just prior to injection of mCRP on days 1, 3 and 5. Blood samples were also drawn on days 12 and 19. The blood samples were analyzed by Fluorescence Activated Cell Sorting (FACS) to determine the percentages of various lymphocyte subsets. Viral titers and the amount of SIV/p27 core protein were also determined. Routine hematological and blood chemistry tests were performed on the blood samples drawn on days 1, 5 and 19 to determine if the animals were suffering any adverse effects as a result of the treatment with mCRP.

FACS was performed on whole blood according to the manufacturer's (Becton Dickinson's) instructions. Briefly, 10–20 $\mu$l of antibody were added to 100 $\mu$l of blood containing EDTA, and the mixture was incubated in the dark for 10 minutes. Then 2 ml of FACS lysing solution (Becton Dickinson) were added, and incubation was continued for 10 minutes at room temperature. Cells were washed once in Minimum Essential Medium containing 5%, fetal calf serum and were then fixed in 0.5% paraformaldehyde. Samples were analyzed on a Becton Dickinson FACScan cytometer.

Levels of T-lymphocytes bearing the CD4 marker are lowered as a result of SIV infection, just as in an HIV-1 infection (Yarchoon et al., 1991). Normal values for monkeys are reported to be about 450 out of 1500 total lymphocytes (30–32%). The Center for Disease Control defined AIDS as that condition with a CD4 lymphocyte count of 200 (14%) or less. Anyone with values as low as this is considered severely immunocompromised.

The percent CD4 lymphocytes in monkey 50B's blood on days 1, 3, 5, 12 and 19 obtained using anti-CD4 monoclonal antibody OKT4a (Ortho) are presented in Table 1 below. This monkey started on day 1 with 22.3% CD4 lymphocytes; thus, its CD4 levels were depressed but were not at an "AIDS level." During treatment (days 3 and 5) the percent CD4 levels increased 17.9% on day 3 and 10.3% on day 5 compared to starting levels on day 1. During the "wash out" period after treatment with mCRP was stopped, the percent CD4 levels fell below the day 1 value.

The results for monkey 2B are also presented in Table 1. Monkey 2B began the study on day 1 with 14.7% CD4 lymphocytes and was, therefore, near the "AIDS level". The percent CD4 level was up 12.2% on day 3 and 17.7% on day 5 after treatment with mCRP compared to the starting level. The percent CD4 level fell below starting levels during the 2-week "washout" period.

A 5% rise in the percent CD4 levels over months of treatment with AZT is considered excellent. Hence, the observed rise of about 10–18% in CD4 levels in both monkeys 2B and 50B within hours of treatment with mCRP is considered extremely good.

TABLE 1

Determination Of CD4 Lymphocytes With OKT4a

| | | CD4 Lymphocytes | | % Change | |
|---|---|---|---|---|---|
| Monkey | Day | Absolute No. CD4 Cells Per $\mu$l* | % CD4 Cells | Absolute No. CD4 Cells Per $\mu$l | % CD4 Cells |
| 2B | 1 | 479 | 14.7 | — | — |
| | 3 | 835 | 16.5 | 74.3 | 12.2 |
| | 5 | 678 | 17.3 | 41.5 | 17.7 |
| | 12 | 529 | 12.4 | 10.4 | −15.6 |
| | 19 | 446 | 12.5 | −6.9 | −15.0 |
| 50B | 1 | 1092 | 22.3 | — | — |
| | 3 | 1330 | 26.3 | 21.8 | 17.9 |
| | 5 | 952 | 24.6 | −12.8 | 10.3 |
| | 12 | 1091 | 20.7 | 0.0 | −7.2 |
| | 19 | 546 | 21.4 | −50.0 | −4.0 |

*Absolute numbers of CD4 lymphocytes determined by multiplying total number of lymphocytes and monocytes by percentage of CD4 cells.

Leu3a, a different monoclonal antibody specific for CD4, was also used to moniter CD4 lymphocytes. The results are presented in Table 2 below. For monkey 50B, the pattern of changes in percent CD4 lymphocytes was similar to that obtained with OKT4a. Monkey 2B exhibited a different pattern. The percent CD4 lymphocytes remained relatively unchanged during the treatment period, but dropped substantially after treatment was stopped. However, the absolute numbers of CD4 lymphocytes per $\mu l$ measure for monkey 2B increased during treatment (days 3 and 5) with mCRP.

TABLE 2

Determination Of CD4 Lymphocytes With Leu3a

| Monkey | Day | CD4 Lymphocytes | | % Change | |
|---|---|---|---|---|---|
| | | Absolute No. CD4 Cells Per $\mu l$* | % CD4 Cells | Absolute No. CD4 Cells Per $\mu l$ | % CD4 Cells |
| 2B | 1 | 572 | 17.6 | — | — |
| | 3 | 827 | 16.4 | 74.3 | -6.8 |
| | 5 | 691 | 17.6 | 41.5 | 0.0 |
| | 12 | 562 | 13.1 | 10.4 | -25.6 |
| | 19 | 491 | 13.8 | -6.9 | -21.6 |
| 50B | 1 | 990 | 20.2 | — | — |
| | 3 | 1382 | 27.4 | 39.6 | 35.6 |
| | 5 | 937 | 24.2 | -5.4 | 19.8 |
| | 12 | 1044 | 19.8 | 5.5 | -2.0 |
| | 19 | 525 | 20.6 | -47.0 | 2.0 |

*Absolute numbers of CD4 lymphocytes determined by multiplying total number of lymphocytes and monocytes by percentage of CD4 cells.

The levels of CD8 lymphocytes were also measured using anti-CD8 antibody Leu2a (Becton Dickinson). The results are presented in Table 3 below. Monkey 2B exhibited increased percentages of CD8 lymphocytes during and after treatment with mCRP a compared to the day 1 levels. Monkey 50B exhibited essentially unchanged percentages of CD8 lumphocytes during the treatment period and decreased percentages after treatment with CRP was stopped.

TABLE 3

Determination Of CD8 Lymphocytes With Leu2a

| Monkey | Day | CD8 Lymphocytes | | % Change | |
|---|---|---|---|---|---|
| | | Absolute No. CD8 Cells Per $\mu l$* | % CD8 Cells | Absolute No. CD8 Cells Per $\mu l$ | % CD8 Cells |
| 2B | 1 | 1926 | 59.1 | — | — |
| | 3 | 3586 | 71.0 | 86.2 | 20.1 |
| | 5 | 2551 | 65.1 | 32.5 | 10.2 |
| | 12 | 2708 | 63.3 | 40.6 | 7.1 |
| | 19 | 2446 | 68.7 | 27.0 | 16.2 |
| 50B | 1 | 2587 | 52.8 | — | — |
| | 3 | 2752 | 54.5 | 6.4 | 3.2 |
| | 5 | 2021 | 52.2 | -21.9 | -1.1 |
| | 12 | 2547 | 48.4 | -1.6 | -8.3 |
| | 19 | 1199 | 47.0 | -53.7 | -11.0 |

*Absolute numbers of CD8 lymphocytes determined by multiplying total number of lymphocytes and monocytes by percentage of CD8 cells.

Finally, the levels of 4B4 lymphocytes were measured. The results are presented in Table 4 below. The 4B4 marker is present on "memory" CD4 lymphocytes which respond to recall antigens. This population of cells is involved with the capacity of the immune system to mount a response to an antigen previously encountered by the immune system. "Native" CD4 cells are those which are involved in "teaching" the immune system to mount a new response to an antigen.

In monkey 50B, the absolute number of 4B4 lymphocytes fluctuated above and below starting levels, but the percentages were constantly elevated during the nineteen-day test period (see Table 4). In monkey 2B, the absolute number of 4B4 lymphocytes was increased throughout the nineteen-day test period, while the percentages of 4B4 lymphocytes decreased and then increased to approximately the starting level (see Table 4).

TABLE 4

Determination Of 4B4 Lymphocytes

| Monkey | Day | 4B4 Lymphocytes | | % Change | |
|---|---|---|---|---|---|
| | | Absolute No. 4B4 Cells Per $\mu l$* | % 4B4 Cells | Absolute No. CD4 Cells Per $\mu l$ | % 4B4 Cells |
| 2B | 1 | 176 | 5.4 | — | — |
| | 3 | 202 | 4.0 | 14.8 | -25.9 |
| | 5 | 187 | 4.8 | 32.5 | -11.1 |
| | 12 | 195 | 4.6 | 40.6 | -15.6 |
| | 19 | 189 | 5.3 | 27.0 | -1.9 |
| 50B | 1 | 269 | 5.5 | — | — |
| | 3 | 310 | 6.1 | 6.4 | 12.0 |
| | 5 | 221 | 5.7 | -21.9 | 4.4 |
| | 12 | 358 | 6.8 | -1.6 | -24.1 |
| | 19 | 176 | 6.9 | -53.7 | 26.3 |

*Absolute numbers of 4B4 lymphocytes determined by multiplying total number of lymphocytes and monocytes by percentage of 4B4 cells.

As noted above, the blood samples drawn on days 1, 5 and 19 were subjected to routine hematological and blood chemistry tests. The results of the hematology and blood chemistries showed no significant changes and no adverse effects as a result of treatment with mCRP. All parameters remained within normal limits during the study.

Finally, no significant clinical abnormalities were observed as a result of treatment with mCRP. Indeed, both monkeys increased in body weight from day 1 to day 19 (the increases were 9% and 15%).

The amount of SIV p27 core protein in the plasma of the monkeys was determined using the COULTER™ SIV Core Ag Assay kit. The assay was performed according to the manufacturer's instructions. Briefly, the SIV Core Ag Assay is an enzyme immunoassay using a murine monoclonal antibody (anti-SIV core antigen p27) coated onto microwells. To perform the assay, 200 $\mu l$ of each sample were added to an antibody-coated microwell, and the microwell strips were covered and incubated for 16–20 hours at room temperature. If present in the sample, the antigen will bind to the antibody-coated coated microwells. After the incubation period, the wells were washed six times with 300 $\mu l$ Wash Buffer. Then, 200 $\mu l$ of a biotinylated human antibody to SIV were added, and the strips were incubated for 1 hour at 37° C. The wells were again washed six times with 300 $\mu l$ Wash Buffer. Next, 200 $\mu l$ conjugated horseradish peroxidase were added to each well, and the strips were incubated for 30 minutes at 37° C. The wells were again washed six times with 300 $\mu l$ Wash Buffer. Next, 200 $\mu l$ tetramethylbenzidine substrate-were added to each well, and the strips were incubated for 30 minutes at room temperature. Color develops from the reaction of the peroxidase with hydrogen peroxide in the presence of the substrate, and the intensity of the color developed is directly proportional to the amount of SIV antigen present in the sample. The reaction was terminated by the addition of 50 µl of Coulter Stopping Reagent, and the strips were read on a microliter plate reader at 450 nm. Values of p27 were obtained in ng/ml by comparison to a standard curve generated from samples supplied with the kit. Positive and negative controls were also run. A negative cutoff value was calculated. This negative cutoff value is the sum of the mean of the negative control wells (diluent only) and a predetermined factor of 0.03. Samples with absorbance values greater than or equal to the cutoff value are considered positive for SIV antigen.

The results are presented in Table 5 below. Plasma antigen levels were below detectable limits in both monkeys at all time points of the study. The mean negative control absorbance was 0.038, and the Coulter negative cutoff was calculated to be 0.068. No absorbance values were greater than the cutoff value.

TABLE 5

Plasma Antigen Levels

| Monkey | Plasma p27 Antigen (ng/ml) | | | | |
|---|---|---|---|---|---|
| | Day 1 | Day 3 | Day 5 | Day 12 | Day 19 |
| 2B | 0.043 | 0.047 | 0.037 | 0.019 | 0.016 |
| 50B | 0.032 | 0.037 | 0.002 | 0.009 | 0.008 |

Virus titrations were performed on blood samples drawn sterilely in preservative-free heparin a follows. Peripheral blood mononuclear cells (PBMC) were separated from the blood using Ficoll-Hypaque. Six four-fold dilutions of PBMC beginning with $3.14 \times 10^4$ cells and six four-fold dilutions of plasma beginning with 50 µl were co-cultured with CEMX174 cells in 96 well microliter plates (total volume 250 µl and total number of CEMX174 cells $2.5 \times 10^4$). Cultures supernatant samples were collected on day 14. Cultures were tested for p27 antigen as described above. All cultures were run in 6 replicates. A negative cutoff point was calculated as described above for each assay plate using uninfected cell culture supernatants as the negative control. Each well was assigned as positive or negative by comparison to the cutoff. Individual virus titers were calculated by the method of Reed and Muench (1938) by summing the replicate values. The negative of the log titer that was thus calculated is plotted versus time in FIGS. 2A and 2B. FIGS. 2A and 2B also show the CD4 lymphocyte levels (using OKT4a).

As can be seen from FIGS. 2A and 2B, there was a dramatic drop in virus titer measured in both PBMC and plasma in each monkey upon treatment with mCRP. The change was greatest for the PBMC titers which decreased approximately 2.0 logs for monkey 50B and 1.5 logs for monkey 2B. The viral titer remained low for about one week after the last dose of mCRP, but then began to climb again. The level of p27 antigen in plasma showed a similar pattern.

From the above, it can be concluded that injection of mCRP into SIV-infected monkeys dramatically decreased cell-associated and plasma SIV virus titers. mCRP also increased the percent CD4 lymphocytes in SIV-infected monkeys during treatment with mCRP. The mCRP treatment did not cause any adverse side effects.

Example 3 mCRP Receptor

While lymphocytes express cytoplasmic and surface CRP, receptors for CRP have been identified on monocyte and neutrophil cells and cell lines. A specific receptor for mCRP has been identified on monocytic cell lines. To determine whether the mCRP receptor represents the same receptor identified above for "CRP", the experiment was performed as follows:

THP-1 cells, a human monocyte cell line, were cultured in RPMI media which was supplemented with 10% fetal calf serum, 2 mM L-glutamine, MEM nonessential amino acids and 1 mM sodium pyruvate. Cells were then plated in 96 well round bottom plates at a density of 500,000 cells/well in a volume of 100 μl.

Serial dilutions of $r_m$CRP in 0.3% gelatin-Phosphate Buffered Saline (+0.2% azide) (i.e, gel-PBS) beginning at 100 μg/ml, were prepared. THP-1 cells were pelleted by centrifugation and the supernatant was removed by gentle pipetting. The cell pellets were resuspended in 100 μl of the $r_m$CRP dilutions and were incubated at room temperature for 2 hours. Following incubation, the cells were washed 3 times with gel-PBS and were then incubated with mCRP-specific monoclonal antibodies 7A8 or 8C10, diluted at 1:1000 in gel-PBS.

The THP-1 cells were washed 3 times with gel-PBS and were then incubated for 1 hour at room temperature with $^{125}$I-labeled goat anti-mouse IgG H+L chain antibody (to a level of 200,000 CPM/well). Cells were again washed 3 times with gel-PBS and the cells were pelleted by centrifugation. Pellets were then solubilized with Hanks Balanced Salt Solution without calcium and magnesium, and containing 10 mM EDTA and 1% Triton X-100. The amount of radiolabel which remained associated with the cell pellet (i.e., bound Ab) was counted in a gamma counter.

The results of the experiment showed that binding of $r_m$CRP to THP-1 cells occurred. Binding was saturable and occurred in a manner consistent with binding to a specific receptor on the cell surface. A morphological change was also noted when $r_m$CRP was added to THP-1 cells. This morphological change is consistent with an effect on the cell cytoskeleton.

In other experiments done at the same time, the addition of $r_m$CRP (but not native CRP) to human macrophages also caused noted morphological changes in the appearance of the macrophages. The significance of these and other data is that they provide evidence that mCRP (and $r_m$CRP) are molecules which can influence the structure of cells of the immune system. This influence is on the cell itself (rather than on the virus), and appears to work by affecting the cell cytoskeleton. By affecting (strengthening) cellular construction a larger barrier to the propagation of the virus. Hence, viral growth is slowed or stopped, and disease does not progress.

Example 4

Distribution of mCRP Inside Cells Containing Type III Intermediate Filaments (Vimentin, Desmin and Glial Fibrillar Acidic Protein [GFAP])

When human tissue sections were stained for the presence of the mCRP antigen using monoclonal anti-mCRP reagents, the cytoplasm of certain cells other than lymphocytes were stained. A frozen tissue section of human skeletal muscle (i.e. myocardium) stained strongly using the anti-mCRP-specific mAb 8C10. A paraffin-embedded human appendix tissue, processed using the antigen retrieval technique and reacted with the anti-mCRP specific mAb 9C9, showed staining of smooth muscle, endothelial cells associated with blood vessels, and, in the midst of a nerve bundle, ganglion cells.

There are many kinds of intermediate filaments which are classified into six different types based on cDNA and amino acid sequencing analyses, peptide mapping and antigenic similarities. Type III intermediate filaments includes vimentin found in cells of mesenchymal derivation or differentiation (cells of the connective tissues and blood i.e. lymphocytes), desmin (found in muscle cells associated with the Z-discs of the sarcomere and the sarcolemmal attachment plaques of striated muscle), and glial Fibrillar acidic protein (GFAP) (found in ganglion cells of nervous tissue).

There is likely a relationship between mCRP and type-III intermediate filaments. Of note, a monoclonal antibody which is widely used in the scientific and medical communities to detect vimentin (mAb anti-vimentin clone V9; ICN Biochemicals), also reacts with mCRP. Conversely, anti-mCRP mAb mCRP 3H12 reacts with mCRP but not vimentin (see included xerox of Western blots). These data suggest that while mCRP is distinct from vimentin, some type of association exists between these two molecules. mCRP may be an intermediate filament associated protein (an IFAP).

Example 5

Data Supporting an Anti-Viral Activity for $r_m$CRP

A.) National Cancer Institute Anti-HIV Screen of recombinant mCRP.

Formulated, mutant recombinant product was sent to the National Cancer Institute for the general anti-HIV-activity screening assay offered by the National Institutes of Health. Both soluble formulated $r_m$CRP protein (which could be prepared at higher concentrations than the biological mCRP) and precipitated protein, were sent. Both forms of $r_m$CRP demonstrated anti-HIV activity, with the soluble form showing an effective concentration 50 (i.e. an $EC_{50}$) at 19.1 μg/ml. In addition to showing a dose-dependent protection from the cytopathic effect of HIV, at the higher concentrations used, both the HIV-infected and the HIV-uninfected cells showed enhanced viability (going up to ~200% of control, untreated cultures.) This assay used the CEM-SS cell line (T4-lymphocytes) and HIV-1 strain of virus. Cell viability is ensured by the addition of the tetrazolium salt, XTT, which forms a blue formazan color in cells undergoing oxidation/reduction reactions (i.e. viable cells). Hence, the % protection is a measure of live, metabolically active cells. In both the HIV-infected and non-infected CEM-SS cells, the metabolic activity of these cells increased as a function of the addition of $r_m$CRP. This is evidence for a direct effect of $r_m$CRP on the cell rather than on the virus. Since it is known that the cell cytoskeleton must be altered to influence cell function (and division), this is consistent with the expectation that the anti-viral activity of $r_m$CRP is based on its effect on the CD4+ cell cytoskeleton; since $r_m$CRP showed the same affect on increasing the metabolic activity of CEM-SS cells in both infected and uninfected cells, this further supports the expectation that the mechanism by which mCRP works is by directly influencing the target cell rather than simply the virus.

B. Follow Up Anti-HIV In Vitro Studies

In vitro testing of the recombinant form of mCRP ($r_m$CRP) using MT-2 cells (another T cell line) and using normal peripheral blood mononuclear cells (PBMCS) as targets for HIV-infection were extended as follows:

Cells were prepared in RPMI media supplemented with 10% fetal calf serum. PBMC stimulatory media was prepared without IL-2. Cells were allowed to incubate for 24 hours in prepared media prior to addition of either the HIV strain H112-5 or the HIV-strain G910.

After 24 hours, cells were harvested and infected with either strain of HIV. To 96 well microtiter plates, dilutions of $r_m$CRP up to 155 μg/ml (prepared in RPMI media) were added in 100 μl volumes. Then either infected or uninfected PBMCs were added at $2 \times 10^5$ cells/well in 100 μl volumes, or infected or uninfected MT-2 cells at $1 \times 10^4$ cells/well in 100 μl volumes were added to the 100 μl volumes were added to the 100 μl $r_m$CRP dilutions already in the wells.

After a six-to-eight day incubation period, cells were examined for morphological changes, for cell viability using the XTT/formazan reagent, and for viral propagation measuring the p24 antigen assay.

Aliquots of cells were treated with reagents and fixatives so that electron microscopy could be performed on treated and untreated samples.

Results:

Morphological changes were caused by $r_m$CRP in both infected and uninfected MT-2 cells.

Morphologically, infected MT-2 cells form syncytia over the incubation period. Syncytia formation is a transient feature of in vitro infection that reflects a phase of maximum virus spreading among cells. Syncytia appear as large, aggregated cells which tend to form and kill the host cell. In a dose-dependent way, $r_m$CRP caused the developing syncytia to break apart. No large cellular aggregates with cytoplasmic "bubbles" were observed. Instead, the MT-2 cells reverted to more normal looking, separate cells of small diameter (see pictures). These morphological changes are consistent with the morphological changes noted when $r_m$CRP (or mCRP) was added to the monocyte cell line TPH-1 cells, to peripheral blood macrophages, or to murine bone-marrow derived megakaryocytes (Potempa et al., 1996). This data is consistent with an interpretation that $r_m$CRP affects the target cell (i.e. the cytoskeleton) which, in turn, affects viral propagation.

Certain $r_m$CRP-treated MT-2-infected cells were kept in culture beyond the 7 day incubation period. After 14 days, approximately 50% of the cells remained alive suggesting the effect of a single dose of $r_m$CRP, added on the first day of culture, could extend cell viability to at least twice that normally expected in this assay system.

Cell viability increased as measured by the XTT/formazan assay, similar to that observed above in the NCI assay. Also, p24 antigen decreased correlated with the increase in cell viability and the revision of cellular morphology.

The viability of uninfected MT-2 cells was unaffected by the incubation of $r_m$CRP at any concentration tested. However, uninfected MT-2 cells form large, serpentine clusters during culture, the addition of $r_m$CRP, in a dose-dependent way, caused such clusters to decrease or eliminate. The resultant distribution of cells was more spread out as is noted with more "normal" cells (e.g. peripheral blood cells grown in culture.)

The $r_m$CRP did aggregate and deposit in the test wells. Evidence of deposited $r_m$CRP was seen in the pictures, especially at the higher concentrations of $r_m$CRP used. This appears to be a novel characteristic of $r_m$CRP which makes it a unique biotherapeutic with an anti-viral activity.

The anti-viral effects of $r_mCRP$ were also demonstrated with peripheral blood monocytes (Kabat et al., 1996). The anti-viral effects were retained even after the addition of $r_mCRP$ was delayed for up to 72 hours after infection.

C.) $r_mCRP$ affects cellular function at the level of the cytoskeleton.

A neutrophil degranulation assay was done to assess the effect of adding $r_mCRP$ to stimulated neutrophils (as a protein which could regulate the inflammatory response).

Fresh polymorphonuclear neutrophils (PMNs) were collected from human donors by centrifugation of EDTA-collected human blood over Polymorphoprep (Nycomed Pharma AS Oslo, Norway) (9 ml EDTA blood, layered over 5 ml Polymorphoprep, 30 minutes at room temperature at 500×g with no brake used at the end of the centrifugation period). The upper layer (containing lymphocytes and platelets) was aspirated and discarded and the lower layer (containing PMNs) was further processed by being underlaid with 7.5 ml of Mono-poly resolving medium (ICN Biomedicals Inc. Aurora, OH) and being centrifuged for 30 minutes. PMNs were collected, divided into aliquots and were diluted into Hanks Balanced Salt Solution (JRH Biosciences, Lenexa, Ks.) and were then centrifuged at 500×g for 10 minutes. The supernate was removed by vacuum aspiration and the cell pellet was resuspended at $2 \times 10^6$ cells/ml in Hanks Balanced Salt Solution.

Serial dilutions of $r_mCRP$ in 50 μl volumes of Hanks balanced salt solution containing 0.5% Human Serum Albumin were added to 100 μl of cells incubated in a round-bottom 96-well microtiter plate for 1 hour at room temperature. The effect of $r_mCRP$ on PMNs was compared to cells incubated with $r_mCRP$ in the presence of a fixed concentration of peptide fMLP (at a final concentration of 1 μM) and cytochalasin B (at a final concentration of 5 μg/ml). FMLP is a stimulatory peptide which is known to activate PMNs. It was used as a positive control. Cytochalasin B is a drug which binds to actin cytoskeleton structures and disrupts cell structure/function. With the cytoskeleton disrupted, the effects of fMLP are maximized (i.e. the release of effector molecules from cytoplasmic granules which occur after PMN activation is not "slowed down" by the presence of an intact cellular cytoskeleton.)

After incubation, PMNs were centrifuged to the bottom of the microtiter plater for 12 minutes at 500×g. 20 μl of supernatant were removed and transferred to a flat bottom microtiter plate. These supernatants were assayed for the presence of myeloperoxidase (MPO) (an enzyme released from PMN granules after activation) using a calorimetric reaction with peroxide and 3,3',5,5'0 tetramethyl benzidine [TMB]). To the 20 μl sample, 75 μl of 0.0027% hydrogen peroxide (prepared by diluting a 30% stock solution in 80 mM potassium phosphate [pH 5.4]) was added. Then, 10 μl of the TMB reagent at a concentration of 3.84 μg/ml in 50% DMF/50% 80 mM potassium phosphate was added to each well. Color development was monitored for 3 minutes at 650 nm.

Results

By itself, $r_mCRP$ did not cause PMN degranulation. However, $r_mCRP$ (but not native CRP) inhibited PMN degranulation caused by a combination of fMLP and cytochalasin B. The inhibition noted was significant and was dose dependent.

This result again provides evidence that $r_mCRP$ has a biological effect in cells which have a disrupted (activated, or diseased) cytoskeleton. By manipulating the cytoskeleton, $r_mCRP$ may elicit its anti-viral effect (and its anti-cancer effect).

D.) In vivo effects of $r_mCRP$ in a human clinical trial

As part of a human clinical trial in HIV-infected men, peripheral blood HIV viral titers were measured as a correlate with $r_mCRP$ therapy, using the PCR technique. Only free viral copies were quantified in the last dose group (i.e., the 2 mg/kg/dose group, intravenously injected on Monday-through-Friday for two consecutive weeks [ten total injections]). In this dose group there were three $r_mCRP$ treated volunteers and one placebo-treated volunteer. A pre-infusion sample was drawn on day 1, and post infusion samples were drawn on days 5, 12 (on the last day of each week of therapy) and on day 22 (10 days after the last infusion).

The following was measured.

TABLE 6

| | HIV-Viral Copy #/ml plasma | | | |
|---|---|---|---|---|
| | Pre-infusion | Day 5 | Day 12 | Day 22 |
| Placebo | 47,300 | 63,880 | 70,364 | 70,700 |
| Volunteer #1 | 41,166 | 20,619 | 16,284 | 37,929 |
| Volunteer #2 | 8,148 | 17,791 | 13,644 | 5,905 |
| Volunteer #3 | 120,488 | 92,329 | 175,444 | 239,301 |

Volunteer #1 began the injection period with viral copies most similar to the placebo-treated volunteer. On days 5 and 12, viral copies in the placebo-treated volunteer increased 35–50% over pre-infusion values. Over the same time period, viral copies in $r_mCRP$-treated volunteer #1 decreased 50–60%. 10 days after therapy was stopped, HIV copies returned to close to pre-infusion levels. This is the same trend in rhesus monkey experiments in initial human clinical trial using the biological mCRP drug.

Volunteer #2 began the infusion period with low level of measurable HIV-RNA (<20% of that level found in either the placebo volunteer or with Volunteer #1). Volunteer #3 began the infusion period with a 2–3-fold higher plasma viral levels. Since all these volunteers were ambulatory and were treated as outpatients, it is possible that the variability in quantified viral levels noted relates to some degree to the stage of disease in each individual. Nonetheless, since the placebo-treated volunteers showed an increase in HIV-RNA levels at all post-infusion time points studied, and since all $r_mCRP$-treated volunteers showed variability in HIV-RNA levels measured (with at least one quantitative measurement in each volunteer being below the starting level), these data support the conclusion that intravenous infusion of $r_mCRP$ in HIV-infected individuals has an effect on the level of virus in the peripheral blood of these individuals.

Example 6

Effects of $r_mCRP$ on Cell Ultrastructure as Measured by Electron Microscopy

MT-2 cells (50,000 cells/well) were grown in culture in the absence and presence of 31.75 μg/ml or 155 μg/ml $r_mCRP$. Cells were either uninfected or were infected with 2000 TCID$_{50}$ of HIV-1/G910. Cells were grown for 8 days at which time they were harvested and prepared for Electron Microscopy (EM) examination using standard fixation and embedding methods (using Epon). Blocks were cut and stained for EM on an Ultracut II ultramicrotome, placed on 200 mesh copper grids and stained with uranyl acetate and lead citrate. Micrographs were taken on a transmission microscope at 1.9 and 2.9 magnification.

The micrograph of an uninfected cell not treated with $r_m$CRP shows a multilobulated nucleus, the presence of a few blebs on the cell periphery, and many lysosomes. When these uninfected cells were grown in the presence of 31.75 µl/ml $r_m$CRP, the nuclear membrane appears to be more well defined, the nucleoli appear more prominent, and the cell Golgi and plasma membrane processes appear to be more pronounced. When these uninfected cells were grown in the presence of 155 µg/ml $r_m$CRP, the nuclear membrane appears defined, localized and darkened, indicating that the nuclear chromatin has condensed into heterochromatin (i.e., that portion of the chromatin material that plays no role in the expression of inborn traits; heterochromatin is inactive in DNA transcription). The nucleolus (site of ribosomal synthesis) is well defined and on one side of the nucleus.

The cytoplasm has numerous endoplasmic reticulum and an expanded number of localized mitochondria. This suggests the cell has reduced DNA transcriptional activity and increased cell metabolic activity. Since viral infectivity and growth depends on transcriptional activities of viral genomes integrated in various ways with a host cell genome, this data supports a belief that $r_m$CRP has anti-viral activity by affecting the structures and functions of the cell that the virus is trying to infect, rather than merely affecting the specific virus trying to infect the cell. As such, $r_m$CRP should be effective against any type of viral infection.

As an ancillary point, mitochondria are thought to be moved around in a cell in connection with microtubule cytoskeleton proteins. That mCRP binds to and influences the intermediate filament cytoskeletal proteins is supported by the fact that the mitochondria are localized to one region of the $r_m$CRP-treated cell. It is known that all cytoskeletal proteins are co-linked such that factors that affect one cytoskeletal protein influence another. This may also explain the effect of $r_m$CRP on cytochalasin (actin-disrupting) treated PMNs as discussed in Section 5C herein.

The micrograph of HIV-infected MT-2 cells grown for 8 days in the absence of $r_m$CRP show the cells to be markedly hydropic (swollen, lysed, close to death). The nuclear material is condensed into non-localized aggregates or is apparently lost from dying cells. There are no cytoplasmic processes of note. Infected cells grown in the presence of 31.75 µm/ml $r_m$CRP show extensively developed filopodia and lamallopodia (thin finger-like cell membrane projections and flattened "palm-like" cell membrane projections, respectively). The nucleus remains multilobuled, but the chromatin material appears to be marginating along the nuclear membrane. There is a single prominent nucleolus and a moderate number of elongated mitochondria. Elongated mitochondria are mitochondria which are active in oxidative metabolism. There are several large iysosomes and more defined endoplasmic reticulum and Golgi. All these changes suggest the cell is in a transition phase from transcriptional activities to increased cell metabolic activities.

HIV-infected cells grown in the presence of 155 µg/ml $r_m$CRP show pronounced heterochromatin condensation and a very prominent nucleolus. Based on viral quantitation and in vitro activity assays, these cells are not only resistant to the cytopathic effect of the HIV virus, but show markedly enhanced metabolic activity. The effects of $r_m$CRP on these infected MT-2 cells is similar to the effects described above for the uninfected cells. Since the effect of $r_m$CRP is on the cell and not directly on the virus, all types of virus are therapeutically targeted.

Example 7

In Vivo Effects of mCRP in a Human Clinical Trial

Three HIV-positive male patients each received 7 infusions of suspension mCRP at a dose of 3 mg/kg body weight over a period of 15–29 days. The suspension mCRP was prepared using partially purified native CRP (Western States Plasma, Fallbrook, Calif.) as the starting material. The native CRP was sterile filtered and further purified by ion exchanged chromatography. The suspended mCRP was then prepared by heating the native CRP to 60° C. for 1 hour in the presence of 1 mM EDTA. The patients received intensive mCRP therapy during the first week (from 3-to-5 injections each), followed by once-a-week infusions for the next two-to-four weeks. Data was gathered over a period of two-to-three months before, during, and after the infusion of mCRP.

Overall, multiple infusions of mCRP were tolerated well with no significant adverse effects. A fever response was noted after all infusions; this was controlled by giving each patient aspirin and Tylenol®. No sign of organ damage (kidney, liver, lung, pancreas, muscle) was noted, and no adverse effect on reticulocytes or leukocytes was noted. There was a drop in the hematocrit of each patient. However, this was not deemed related to mCRP therapy. Total lymphocyte counts, CD4+ lymphocyte counts and CD8+ lymphocyte counts, increased in all patients correlating with mCRP therapy. Serum electrolytes, enzymes, proteins and other factors (e.g., glucose, triglycerides, cholesterol, uric acid, BUN, creatinine) all remained within normal limits throughout the study. Both intrinsic and extrinsic coagulation pathways were unaffected by intravenous infusion of mCRP.

Both PBMC and plasma HIV-RNA titer was measured using PCR technology. As shown in the Table below, Patient #1 showed a decrease in both PBMC-associated and plasma viral titers quantified during those days of mCRP therapy (days 5 and 8). PBMC viral titers decreased from 120,000 HIV mRNA copies/µg total RNA to 13,770 HIV mRNA copies/µg total RNA on Study Day 5. Levels remained low at 31,967 HIV mRNA copies/µg total RNA on day 8, and rebounded to 293,852 HIV mRNA copies/µg total RNA two weeks after therapy had ended. The number of HIV RNA molecules/ml of plasma decreased from 115,200 copies/ml to 72,000 copies/ml during the period of therapy, and rebounded to 108,000 copies/ml on study day 29.

Patient #2 showed a similar drop in PBMC-associated viral titer during the therapy period, dropping from 23,000 HIV mRNA copies/µg total RNA to undetectable levels (i.e. <5,000) during the period of mCRP therapy. Plasma viral titer also decreased from 114,000 molecules of HIV-RNA/ml of plasma to 14,000 molecules/ml on day 8 of the study period.

In Patient #3, no measurable PBMC HIV RNA was detected throughout the study period. Plasma HIV RNA titer results were variable.

TABLE 7

| | Patient #1 | | Patient #2 | | Patient #3 | |
|---|---|---|---|---|---|---|
| | PBMC HIV RNA (HIV mRNA copies/µg total RNA) | Plasma HIV RNA (molecules of HIV RNA/ml) | PBMC HIV RNA (HIV mRNA copies/µg total RNA) | Plasma HIV RNA (molecules of HIV RNA/ml) | PBMC HIV RNA (HIV Mrna copies/µg total RNA) | Plasma HIV RNA (molecules of HIV RNA/ml) |
| Study Day 1 | 120,000 | 115,200 | 23,000 | 114,000 | <5,000 | 10,800 |
| Study Day 2 | 13,770 | 72,000 | <5,000 | 126,000 | <5,000 | 96,000 |
| Study Day 8 | 31,967 | 72,000 | <5,000 | 14,000 | <5,000 | 126,000 |
| Study Day 29 | 293,852 | 108,000 | 42,000 | 111,600 | <5,000 | 32,400 |

Treatment days were Days 1 through 5, 8 and 15. Patients received intravenous injections of suspended mCRP at 3 mg/kg/dose in saline.

These data are consistent with those results observed in the Rhesus monkey SIV model. Intravenous infusions of mCRP correlate with a drop in both PBMC and plasma HIV titer. After infusions were stopped, HIV titers began rebounding to pre-infusion levels.

DOCUMENTS CITED

Ballou et al. *Clin. Exp. Immunol*, 84:329–335 (1991).
Atono et al., *Gastroenterologia Japonica*, 24 655–662 (1989).
Ballou et al., *J. Lab. Clin. Med.*, 115:332–338 (1990).
Bama et al., *Cancer Research*, 44:305–310 (1984).
Bray et al., *Clin. Immunol. Newsletter*, 8:137–140 (1987).
Busso et al., *AIDS* 5:1425–1432 (1991).
Chase, "Doctors and Patients Hope AZT Will Help Stave Off AIDS," *Wall Street Journal*, Apr. 28, 1988, page 14, col. 1.
*Chem. Eng. News*, Oct. 14, 1991, at 17.
Chu et al., *Proc. Amer. Acad. Cancer Res.*, 28:344a (1987).
Chu et al., *Proc. Amer. Acad. Cancer Res.*, 29:371a (1988).
Chudwin et al., *J. Allergy Clin. Immunol.*, 77:216a (1986).
Dagani, *Chem. Eng. News*, Nov. 23, 1987, at 41–49.
Deodhar et al., *Cancer Research*, 42:5084–5088 (1982).
DuClos, *J. Immunol*, 143:2553–2559 (1989).
Fauci et al., *Ann. Intern. Med.*, 114:678–693 (1991).
Fauci et al., *Science.*, 2392:617–622 (1988).
Gotschlich *Ann. N.Y Acad. Sci.*, 557:9–18 (1989).
Gupta et al., *J. Immunol.*, 137:2173–2179 (1986).
Hokama et al., *J. Bacteriology*, 83:1017–1024 (1962).
Horowitz et al., *J. Immunol.*, 138:2498–2603 (1987).
Hu et al., *Biochem*, 25:7834–7839 (1986).
Hu et al., *J. Biol. Chem.*, 263:1500–1504 (1988).
James et al., *Dissertation Abstracts International*, 41/08-B, 2963 (1980).
Kabat et al. AIDS Clinical Trial Group Meeting July 1996, Abstract #14.
Kempka et al., *J. Immunol.*, 144:1004–1009 (1990).
Khayyri et al. *Cell Immunol*, 155.457–475 (1994).
Kilpatrick and Volanakis, *Immunol. Res.*, 10:43–53 (1991).
Kilpatrick and Volanakis, *J. Immunol.*, 134:3364–3370 (1985).
Kindmark, *Clin. Exp. Immunol.*, 8:941–948 (1971).
Lei et al., *J. Biol. Chem.*, 260:13377–13383 (1985).
Mantzouranis et al., *Ped. Res.*, 18:260a (1984).
Mold et al., *Infection and Immunity*, 38:392–395 (1982).
Montefiori et al., *Proc. Nat'l Acad. Sci. U.S.A.*, 84:2985–2989 (1987).
Motie, et al. *J. Immunol.*, 156:4435–4441 (1996).
Murphy et al., *J. Exp. Med.*, 173; 495–498 (1991).
Nakayama et al., *Clin. Exp. Immunol.*, 54:319–326 (1983).
Nakayama et al., *J. Immunol.*, 132:1336–1340 (1984).
Pepys et al., *Clin. Exp. Immunol*, 97:152–157 (1994).
Potempa et al., *Exp'l Hematol*, 24:258–264 (1996).
Potempa et al., *FASEB J.*, 2:731a (1988).
Potempa et al., *FASEB J.*, 10:1332a (1996).
Potempa et al., *Inflammation*, 12:391–405 (1988).
Potempa et al., *Mol. Immunol.*, 20:1165–1175 (1983).
Potempa et al., *Mol. Immunol.*, 24:531–541 (1987).
Potempa et al., *Proc. Amer. Acad. Cancer Res.*, 28:344a (1987).
Potempa et al., *Prot. Biol. Fluids*, 34:287–290 (1986).
Putto et al., *Archives of Disease in Childhood*, 61:24–29 (1986).
Reed and Muench, *Amer. J. Hygiene*, 27:493 (1938).
Rees et al., *Fed. Proc.*, 45:263a (1986).
Samols and Hu, *Prot Biol. Fluids*, 34:263–266 (1986).
Samols et al., *Biochem. J.*, 227, 759–765 (1985).
Shoeman et al., *Medical Hypotheses*, 37:137–150 (1992).
Samberg et al., *Cellular Immunology*, 116:86–98 (1989).
Tablin et al., *J. of Cell Scence* 97:59–70.
Tebo et al., *J. Immunol.*, 144:231–238 (1990).
Thombre et al., *Cancer Immunol. Immunother.*, 16:145–150 (1984).
Tillett and Francis *J. Exp. Med.*, 52:561–571 (1930).
Vaith, et al., *Int'l Archives Allergy & Clin. Immunol*, 111:107–117 (1996).
Volanakis et al., *J. Immunol.*, 113:9–17 (1978).
Weislow et al., *J. Natl. Cancer Inst.*, 81:577–586 (1989).
Whitehead et al., *Biochem. J.*, 266:83–90 (1990).
Woo et al., *J. Biol. Chem.*, 260:13384–13388 (1985).
Xia et al., *FASEB J.*, 5:1628a (1991).
Yarchoan et al., *Anal Intern. Med.*, 115:184–89 (1991).
Yarchoan et al., *Immunol. Today*, 11:327–333 (1990).
Ying et al., *J. Immunol.*, 143:221–228 (1989).
Ying et al., *Mol. Immunol*, 29:677–687 (1992).

I claim:

1. A method of treating a viral infection in a mammal caused by Epstein-Barr virus, the method comprising administering an effective amount of modified C-reactive protein to the mammal.

2. A method of treating a viral infection in a mammal caused by Herpes simplex virus, the method comprising administering an effective amount of modified C-reactive protein to the mammal.

* * * * *

UNITED STATES PATENT AND TRADEMARK OFFICE
CERTIFICATE OF CORRECTION

PATENT NO. : 6,239,099 B1  
DATED : May 29, 2001  
INVENTOR(S) : Potempa et al.

Page 1 of 1

It is certified that error appears in the above-identified patent and that said Letters Patent is hereby corrected as shown below:

Title page,
Item [63], "Related U.S. Application Data",
Line 1, please delete "Continuation" and insert -- Continuation-in-part -- therefor.
Line 4, please delete "continuation" and insert -- continuation-in-part -- therefor.

Signed and Sealed this

Twenty-second Day of January, 2002

*Attest:*

*Attesting Officer*

JAMES E. ROGAN
*Director of the United States Patent and Trademark Office*